US007957935B2

(12) United States Patent
Nishida et al.

(10) Patent No.: US 7,957,935 B2
(45) Date of Patent: Jun. 7, 2011

(54) ANALYZER AND METHOD OF RESTARTING SAMPLE MEASUREMENT

(75) Inventors: Tomoyuki Nishida, Ashiya (JP); Yuji Wakamiya, Kobe (JP); Hisato Takehara, Kobe (JP)

(73) Assignee: Sysmex Corporation, Hyogo (JP)

( * ) Notice: Subject to any disclaimer, the term of this patent is extended or adjusted under 35 U.S.C. 154(b) by 65 days.

(21) Appl. No.: 12/254,583

(22) Filed: Oct. 20, 2008

(65) Prior Publication Data

US 2009/0292492 A1 Nov. 26, 2009

(30) Foreign Application Priority Data

May 22, 2008 (JP) ................................. 2008-133825

(51) Int. Cl.
*G06F 11/00* (2006.01)
*G01N 35/00* (2006.01)
(52) U.S. Cl. ......................................... 702/182; 422/67
(58) Field of Classification Search .................. 702/182, 702/185, 85; 422/64, 67
See application file for complete search history.

(56) References Cited

U.S. PATENT DOCUMENTS

| 7,707,010 B2 * | 4/2010 | Wakamiya et al. ........... 702/187 |
| 2005/0036913 A1 * | 2/2005 | Yamakawa et al. ............ 422/65 |
| 2007/0172390 A1 | 7/2007 | Ootani et al. |

FOREIGN PATENT DOCUMENTS

JP 2006-170868 A 6/2006

* cited by examiner

*Primary Examiner* — Bryan Bui
(74) *Attorney, Agent, or Firm* — Sughrue Mion, PLLC

(57) ABSTRACT

An analyzer includes a specimen preparing section for preparing a measuring specimen including a specimen and a reagent, the specimen preparing section including a plurality of units; a detecting section for detecting a predetermined component from the specimen; a start command receiver for receiving a starting measurement instruction; a measurement controller for controlling the units and the detecting section when the starting measurement instruction is received; an error detecting section for detecting an error in the operations of the units; a measurement abort controller for stopping the operations of the units when the error is detected; a restart command receiver for receiving a restart measurement instruction after the abortion of the measurement; and a remeasurement controller for moving the units to initial positions thereof and controlling the units and the detecting section when the restarting measurement instruction is received is disclosed. A method of restarting sample measurement is also disclosed.

20 Claims, 12 Drawing Sheets

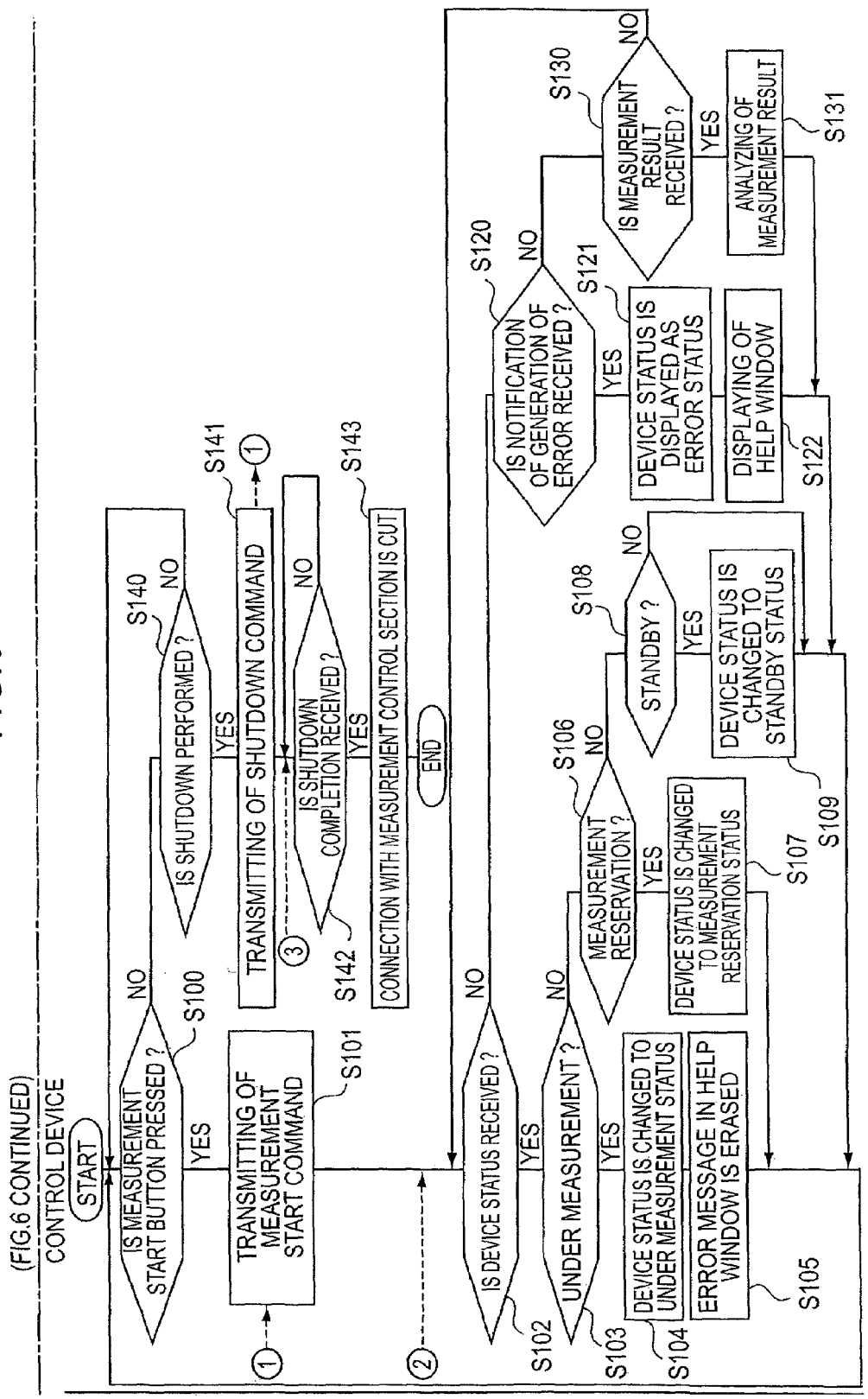

ANALYZER AND METHOD OF RESTARTING SAMPLE MEASUREMENT

FIELD OF THE INVENTION

The present invention relates to an analyzer and a method in which a user can easily and rapidly restart measurement when an error occurs in the analyzer.

BACKGROUND

Analyzers for subjecting a sample such as blood or urine to measurement are used in hospitals and inspection centers. In recent years, the analyzers have increased in size and been mounted with a number of units to improve processing capabilities. For these reason, in some cases, a plurality of errors are simultaneously generated.

JP-A-2006-170868 discloses an analyzer which displays a plurality of generated errors in tabular form so as to allow even a user having no specific knowledge and technique to perform a recovery operation for the errors. In addition, in the analyzer disclosed in this JP-A-2006-170868, the content of a recovery method can be edited in accordance to a use status of the user such that the user can easily understand a ranking of importance of the errors displayed in the tabular form and the recovery method for the errors.

However, in the technique of JP-A-2006-170868, when the errors are generated in the analyzer, the user selects the error to be recovered from a window on which the errors are displayed and displays a trouble shooting window to recover the selected error in accordance with a recovery procedure displayed in a dialog form in the window. Further, when a plurality of the errors are simultaneously generated in the analyzer, the user have to perform the above recovery operation for the generated errors. Accordingly, the operation is complicated for the user and requires considerable time.

The invention is contrived in view of such circumstances and an object of the invention is to provide an analyzer in which measurement can be easily and rapidly restarted when a plurality of errors are generated in the analyzer.

SUMMARY OF THE INVENTION

The scope of the present invention is defined solely by the appended claims, and is not affected to any degree by the statements within this summary.

A first aspect of the present invention is an analyzer comprising: a specimen preparing section for preparing a measuring specimen including a specimen and a reagent, the specimen preparing section including a plurality of units performing predetermined operations; a detecting section for detecting a predetermined component from the measuring specimen prepared by the specimen preparing section; a start command receiver for receiving an instruction for starting measurement operations including preparing the measuring specimen by the specimen preparing section and detecting the predetermined component of the measuring specimen by the detecting section; a measurement controller for controlling the plurality of units and the detecting section so as to perform the measurement operations when the start command receiver receives the instruction for starting the measurement operations; an error detecting section for detecting an error in the operations of the plurality of units; a measurement abort controller for stopping the operations of the plurality of units when the error detecting section detects the error; a restart command receiver for receiving an instruction for restarting the measurement operations after the measurement abort controller stops the measurement operations; and a remeasurement controller for moving the plurality of units to initial positions thereof and then controlling the plurality of units and the detecting section so as to restart the measurement operations when the restart command receiver receives the instruction for restarting the measurement operations.

A second aspect of the present invention is a method of restarting sample measurement by an analyzer including a plurality of units, the method comprising: (a) receiving an instruction for staring measurement operations including preparing a measuring specimen and detecting a predetermined component from the measuring specimen; (b) performing the measurement operations by the plurality of units when the instruction for staring the measurement operations is received; (c) detecting an error in operations of the plurality of units during the measurement operations; (d) stopping the measurement operations when the error is detected in the operations of the plurality of units; (e) receiving an instruction for restarting the measurement operations; and (f) moving the plurality of units to initial positions thereof and restarting the measurement operations when the instruction for restarting the measurement operations is received.

A third aspect of the present invention is an analyzer comprising: a specimen preparing section for preparing a measuring specimen including a specimen and a reagent, the specimen preparing section including a plurality of units performing predetermined operations; a detecting section for detecting a predetermined component from the measuring specimen prepared by the specimen preparing section; an error detecting section for detecting an error in the operations of the plurality of units; and a controller, including a memory under control of a processor, the memory storing instructions enabling the processor to carry out operations, comprising: (a) receiving an instruction for starting measurement operations including preparing the measuring specimen and detecting the predetermined component from the measuring specimen; (b) performing the measurement operations by the plurality of units when the instruction for starting the measurement operations is received; (c) stopping the measurement operations when the error is detected in the operations of the plurality of units; (d) receiving an instruction for restarting the measurement operations; and (e) moving the plurality of units to initial positions thereof and restarting the measurement operations when the instruction for restarting the measurement operations is received.

DETAILED DESCRIPTION OF THE PREFERRED EMBODIMENTS

The preferred embodiments of the present invention will be described hereinafter with reference to the drawings.

Overall Configuration of Device

Figure 1:
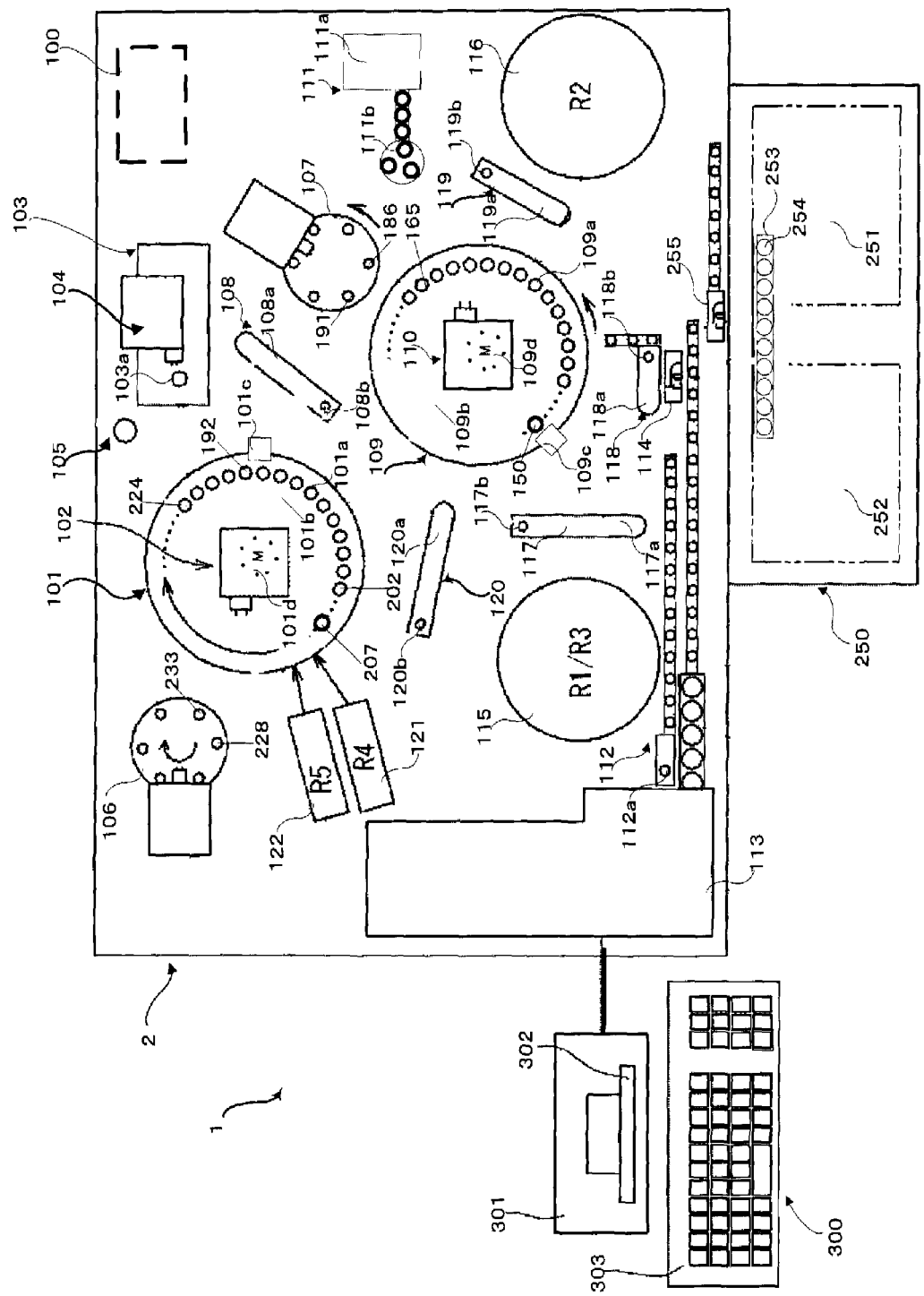
FIG. 1 is an example of an overall configuration diagram of an analyzer according to a first embodiment.

FIG. 1 is a plan explanatory diagram illustrating the overall configuration of an immunological analyzer (sample analyzer) according to an embodiment of the invention.

The immunological analyzer 1 is a device for inspecting various measuring items such as hepatitis B, hepatitis C, tumor marker, and thyroid hormone by using a sample (specimen) such as blood. As illustrated in FIG. 1, the immunological analyzer 1 is configured by a measuring unit 2 including a plurality of mechanisms (components) and a control device 300 as a data processing unit which is electrically connected to the measuring unit 2.

With the immunological analyzer 1, capture antibodies (reagent R1) bound to antigens included in the sample such as blood as a measuring target are bound to magnetic particles (reagent R2) and then the bound antigens, capture antibodies and magnetic particles are drawn to a magnet of a first BF (Bound Free) separating section 107 to remove the reagent R1 including the unreacted (Free) capture antibodies. In addition, the antigens bound to the magnetic particles are bound to labeled antibodies (reagent R3) and then the bound magnetic particles, antigens and labeled antibodies are drawn to a magnet of a second BF separating section 106 to remove the reagent R3 including the unreacted (Free) labeled antibodies. Further, luminescent substrates (reagent R5) emitting light in the course of the reaction with the labeled antibodies are added and then an amount of luminescence generated by the reaction of the labeled antibodies with the luminescent substrates is measured. Through such a course, the antigens included in the sample bound to the labeled antibodies are quantitatively measured.

Configuration of Measuring Unit

The measuring unit 2 mainly has a measurement control section 100, a second reaction section 101, a second shaking catcher 102, a detecting section 103, a detecting section catcher 104, a discarding section 105, the second BF separating section 106, the first BF separating section 107, a transporting mechanism 108, a first reaction section 109, a first shaking catcher 110, a cuvette supply device 111, a tip transporting section 112, a pipette tip supply device 113, a tip removing section 114, a reagent R1/R3 mounting section 115, a reagent R2 mounting section 116, a reagent R1 dispensing arm 117, a sample dispensing arm 118, a reagent R2 dispensing arm 119, a reagent R3 dispensing arm 120, a reagent R4 supply section 121, a reagent R5 supply section 122, a transporting section 250 and a bar-code reader 255. The mechanisms of the measuring unit 2 have respective initial positions and the measurement control section 100 controls the mechanisms to move the mechanisms from the respective initial positions to a predetermined pulse or a predetermined position.

The mechanisms of the measuring unit 2 can properly employ known configurations. However, hereinafter, the configurations thereof will be simply described with reference to FIG. 1.

Figure 4:
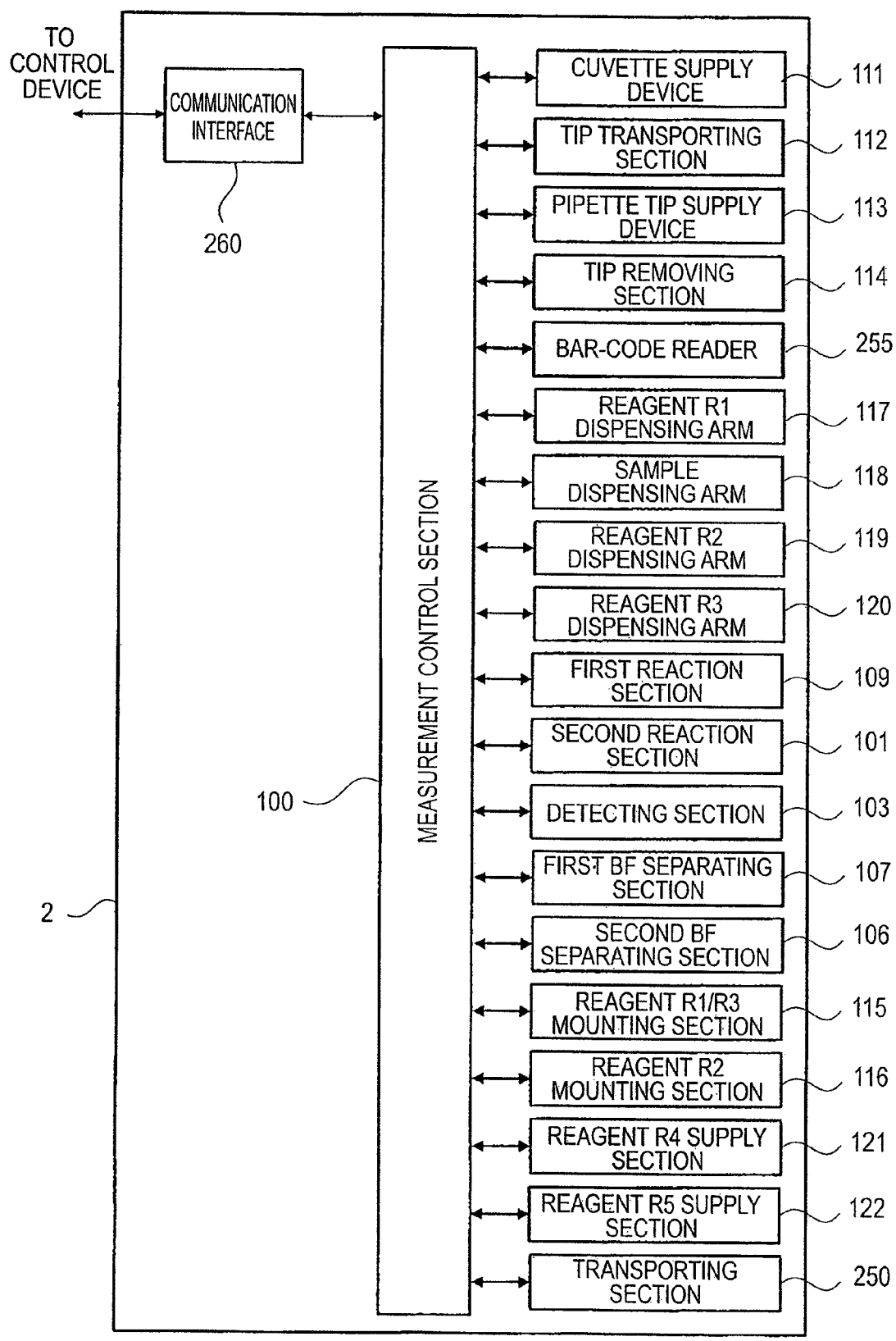
FIG. 4 is a hardware configuration diagram of a measurement control section.

The measurement control section 100 has a CPU, a RAM, and a ROM. As illustrated in FIG. 4, the measurement control section 100 receives measurement information from the control device 300, transmits a measurement result to the control device 300 and notifies the control device 300 of an error through a communication interface 260 using Ethernet (registered trade name) as well as to control the mechanisms.

Figure 2:
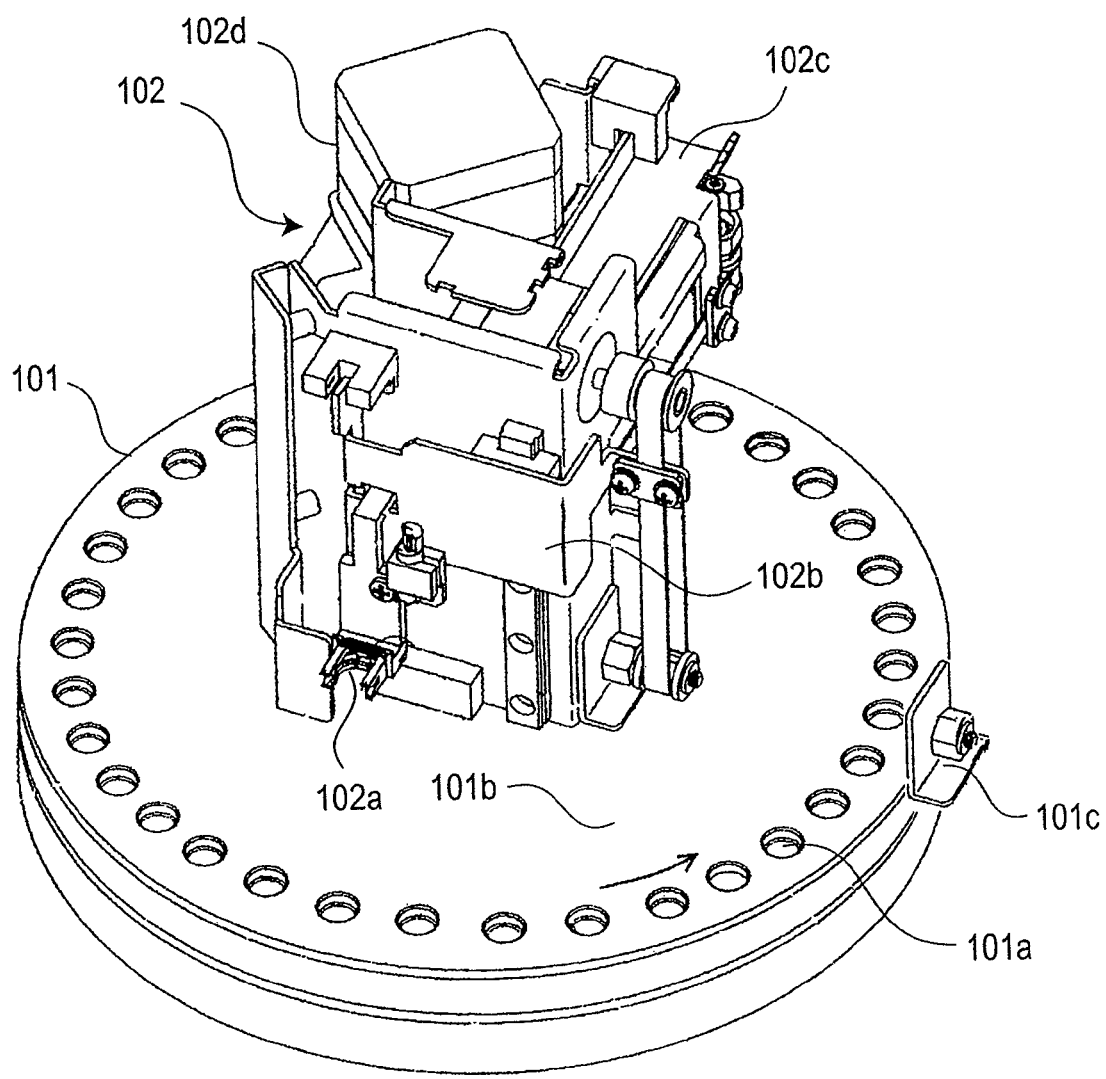
FIG. 2 is a hardware configuration diagram of a second reaction section.

As illustrated in FIG. 2, the second reaction section 101 has a rotation table section 101b, a sensor 101c and a motor 101d.

The rotation table section 101b has an annular upper surface and a plurality of holding holes 101a are equally spaced so as to form an annulus ring coaxial with the rotation table section 101b.

The sensor 101c is provided to detect whether a cuvette is present at the holding hole 101a positioned in front of the sensor 101c. In addition, the rotation table section 101b has an initial position and is provided with a sensor (not shown) for detecting that the rotation table section is returned to the initial position. When receiving an instruction for measurement start and receiving an instruction for measurement restart after abort of the measurement operations by an error, the measurement control section 100 returns the rotation table section 101b to the initial position and controls the rotation table section 101b so as to perform a predetermined measurement operation.

The motor 101d is mounted under the rotation table section 101b and is configured so as to rotate the rotation table section 101b by a predetermined angle at predetermined intervals. The devices of the immunological analyzer 1 (reagent R4 dispensing arm 121, reagent R5 dispensing arm 122 and the like) are controlled so as to be operated at a timing at which the cuvette held in the holding hole 101a is transported to a predetermined position by the rotation table section 101b.

As illustrated in FIG. 2, the second shaking catcher 102 has a shaking section 102a, a vertical movement mechanism section 102b, a horizontal movement mechanism section 102c and a rotation mechanism section 102d. The shaking section 102a has a function of grasping and shaking the cuvette. The vertical movement mechanism section 102b has a function of vertically moving the shaking section 102a. The horizontal movement mechanism section 102c has a function of horizontally moving the shaking section 102a and the vertical movement mechanism section 102b. The rotation mechanism section 102d has a function of rotating the shaking section 102a, the vertical movement mechanism section 102b and the horizontal movement mechanism section 102c around the center of the rotation table section 101b of the second reaction section 101. Further, the second shaking catcher 102 has initial positions in a vertical direction, a horizontal direction and a rotational direction and is provided with sensors (not shown). The sensors detect that the second shaking catcher 102 is returned to the initial positions. When receiving an instruction for measurement start and receiving an instruction for measurement restart after abort of the measurement operations by an error, the measurement control section 100 returns the second shaking catcher 102 to the initial positions in the vertical direction, horizontal direction and rotational direction and then controls the second shaking catcher 102 so as to perform a predetermined measurement operation.

That is, the second shaking catcher 102 has a function of grasping the cuvette put at the holding hole 101a of the rotation table section 101b of the second reaction section 101 and moving the grasped cuvette upward to shake the specimen in the cuvette. The second shaking catcher 102 also has a function of transporting the cuvette held in the holding hole 101a positioned at a position 202 on the rotation table section 101b to a position 228 on the second BF separating section 106. Further, the second shaking catcher 102 has a function of transporting the cuvette held in the holding hole positioned at a position 233 on the second BF separating section 106 to the holding hole 101a at a position 207 on the rotation table section 101b.

Returning to FIG. 1, the detecting section 103 has a mounting section 103a on which the cuvette to be subjected to photometry is mounted. By using a photo multiplier tube, the detecting section photometrically measures light emitted from the specimen in the cuvette mounted on the mounting section 103a and measures an amount of the antigens included in the sample.

Figure 3:
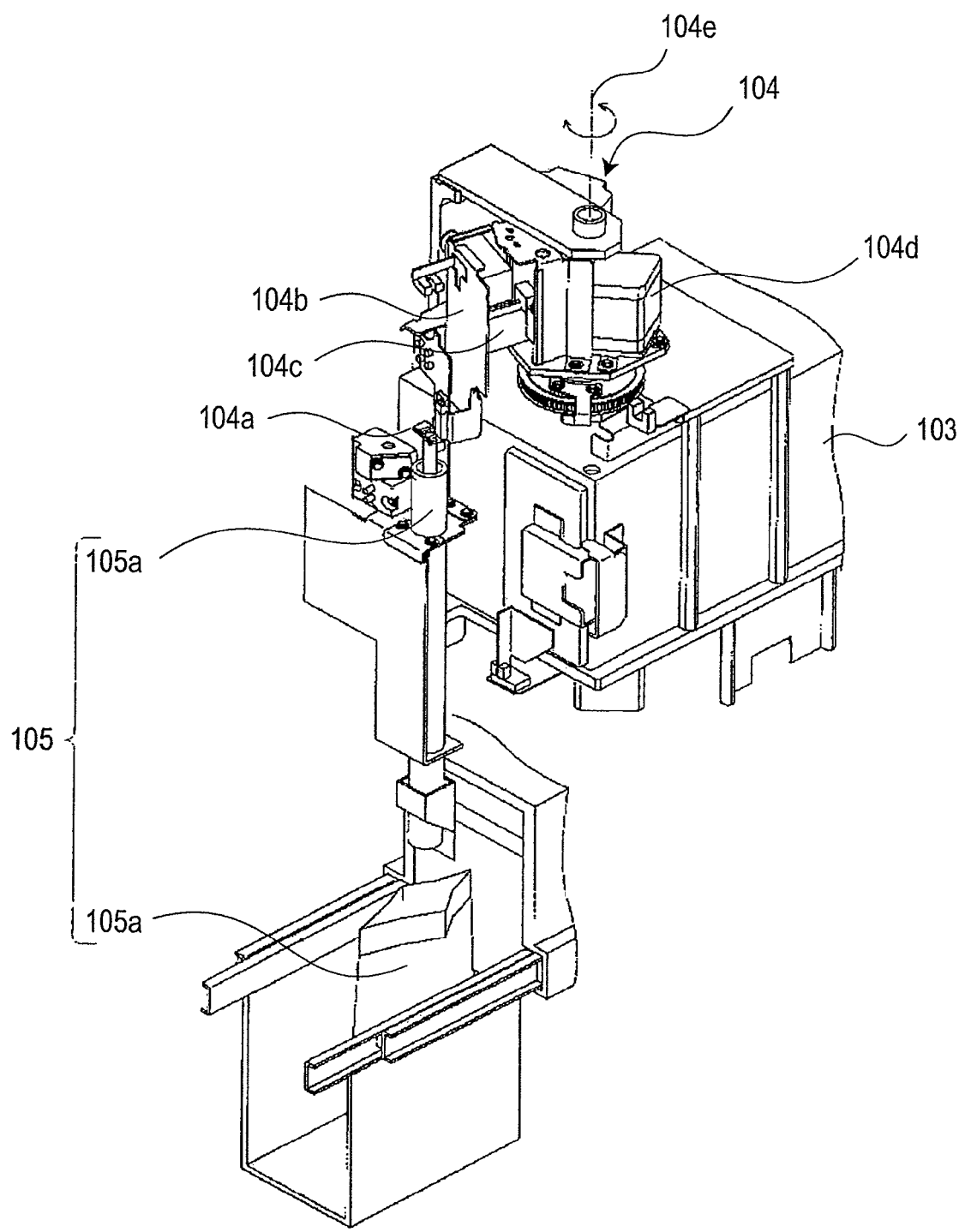
FIG. 3 is a hardware configuration diagram of a detecting section and a discarding member.

As illustrated in FIG. 3, the detecting section catcher 104 has a shaking section 104a, a vertical movement mechanism section 104b, a horizontal movement mechanism section 104c and a rotation mechanism section 104d.

The shaking section 104a has a function of grasping the cuvette and moving the grasped cuvette upward to be shaken. The vertical movement mechanism section 104b has a function of vertically moving the shaking section 104a. The horizontal movement mechanism section 104c has a function of horizontally moving the shaking section 104a and the vertical movement mechanism section 104b. The rotation movement mechanism section 104d has a function of rotating movement the shaking section 104a, the vertical movement mechanism section 104b and the horizontal movement mechanism section 104c around a shaft 104e. Further, the detecting section catcher 104 has initial positions in a vertical direction, a horizontal direction and a rotational direction and is provided with sensors (not shown) The sensors detect that the detecting section catcher 104 is returned to the initial positions. When receiving an instruction for measurement start and receiving an instruction for measurement restart after abort of the measurement operations by an error, the measurement control section 100 returns the detecting section catcher 104 to the initial positions in the vertical direction, horizontal direction and rotational direction and then controls the detecting section catcher 104 so as to perform a predetermined measurement operation.

That is, the detecting section catcher 104 has a function of grasping the cuvette held in the holding hole 101a positioned at a position 224 on the rotation table section 101b of the second reaction section 101 and moving the grasped cuvette upward to shake the specimen in the cuvette and mount the cuvette on the mounting section 103a of the detecting section 103. Further, the detecting section catcher 104 has a function of discarding the cuvette on the mounting section 103a of the detecting section 103 to the discarding section 105 when detection is completed in the cuvette on the mounting section 103a of the detecting section 103.

The detecting section catcher 104 also has a function of grasping the cuvette held in the holding hole 101a positioned at the position 224 on the rotation table section 101b of the second reaction section 101 and moving the grasped cuvette upward to discard the cuvette to the discarding section 105 when the discard operation of the cuvette is performed.

FIG. 3 is a perspective view of the detecting section catcher 104 and the discarding section 105. The discarding section 105 has a discarding member 105a and a discarding bag 105b. After the specimen in the cuvette is subjected to photometric measurement by the detecting section 103, the cuvette on the mounting section 103a of the detecting section 103 is discarded to the discarding bag 105b by the detecting section catcher 104 through the hole of the discarding member 105a.

Returning to FIG. 1, the second BF separating section 106 is provided to separate the unreacted reagent R3 (unnecessary components) and the magnetic particles from the specimen in the cuvette transported to the second BF separating section 106 from the second reaction section 101 by the second shaking catcher 102. The cuvette on the second BF separating section 106 from which the unreacted reagent R3 is separated is transported again to the second reaction section 101 by the second shaking catcher 102.

The first BF separating section 107 has the same configuration as the second BF separating section 106 and is provided to separate the unreacted reagent R1 (unnecessary components) and the magnetic particles from the specimen in the cuvette transported from the first reaction section 109 by the first shaking catcher 110. The cuvette on the first BF separating section 107 from which the unreacted reagent R1 is separated is transported to the second reaction section 101 by the transporting mechanism 108 to be described later.

The transporting mechanism 108 has an arm section 108a (having the same configuration as the shaking section 102a of the second shaking catcher 102 of FIG. 2) having a cuvette grasping section at a tip end thereof and a shaft 108b acting as a center when the arm section 108a is rotated. The transporting mechanism 108 grasps the cuvette on the first BF separating section 107 by the cuvette grasping section at the tip end of the arm and moves the grasped cuvette upward to be transported to the rotation table section 101b of the second reaction section 101.

The first reaction section 109 has the same configuration as the second reaction section 101 and has a rotation table section 109b, a sensor 109c and a motor 109d.

The rotation table section 109b has an annular upper surface and a plurality of holding holes 109a are equally spaced so as to form an annulus ring coaxial with the rotation table section 109b.

The sensor 109c is provided to detect whether a cuvette is present at the holding hole 109a positioned in front of the sensor 109c.

The motor 109d is mounted under the rotation table section 109b and is configured so as to rotate the rotation table section 109b by a predetermined angle at predetermined intervals. The devices of the immunological analyzer 1 (reagent R1 dispensing arm 117, reagent R2 dispensing arm 119 and the like) are controlled so as to be operated at a timing at which the cuvette held in the holding hole 109a is transported to a predetermined position by the rotation table section 109b.

The first shaking catcher 110 has the same configuration as the second shaking catcher, and has a function of supplying a cuvette to the holding hole 109a positioned at a position 150 on the rotation table section 109b of the first reaction section 109 from the cuvette supply device 111 to be described later, grasping the cuvette held in the holding hole 109a and moving the grasped cuvette upward to shake the specimen in the cuvette. The first shaking catcher also has a function of transporting the cuvette held in the holding hole 109a positioned at a position 165 on the rotation table section 109b of the first reaction section 109 to a holding hole positioned at a position 186 on the first BF separating section 107.

The cuvette supply device 111 has a cuvette injecting portion 111a and a cuvette providing table 111b.

An user of the immunological analyzer 1 supplies cuvettes from the cuvette injecting portion 111a and the cuvettes in the cuvette injecting portion 111a are supplied to the cuvette providing table 111b one by one. By the first shaking catcher 110, the cuvettes on the cuvette providing table 111b are set in the predetermined holding holes 109a on the rotation table section 109b of the first reaction section 109.

The pipette tip supply device 113 has a function of supplying an injected pipette tip to a tip mounting section 112a of the tip transporting section 112 one by one.

The tip removing section 114 is provided to remove the pipette tip mounted on the sample dispensing arm 118 to be described later.

The reagent R1/R3 mounting section 115 is mounted with a reagent container containing the reagent R1 including the capture antibodies and a reagent container containing the reagent R3 containing the reagent R3 including the labeled antibodies.

The reagent R2 mounting section 116 is mounted with a reagent container containing the reagent R2 including the magnetic particles.

The reagent R1 dispensing arm 117 is provided with an arm section 117a and a shaft 117b.

A nozzle for suctioning and ejecting the reagent is attached to a tip end of the arm section 117a and is configured so as to be rotated around the shaft 117b and be moved in an up-and-down direction. In addition, the reagent R1 dispensing arm 117 has initial positions in a rotational direction and an up-and-down direction and is provided with sensors (not shown). The sensors detect that the reagent R1 dispensing arm 117 is returned to the initial positions. When receiving an instruction for measurement start and receiving an instruction for measurement restart after abort of the measurement operations by an error, the measurement control section 100 returns the reagent R1 dispensing arm 117 to the initial positions in the rotational direction and the up-and-down direction and then controls the reagent R1 dispensing arm 117 so as to perform a predetermined measurement operation.

The reagent R1 dispensing arm 117 has a function of suctioning the reagent R1 in the reagent container mounted on the reagent R1/R3 mounting section 115 and ejecting the suctioned reagent R1 to the cuvette held in the predetermined holding hole 109a on the rotation table section 109b of the first reaction section 109.

The sample dispensing arm 118 is provided with an arm section 118a and a shaft 118b.

A nozzle for suctioning and ejecting the sample is attached to a tip end of the arm section 118a, and a pipette tip transported by the tip transporting section 112 is mounted on a tip end of the nozzle section and is configured so as to be rotated around the shaft 118b and be moved in an up-and-down direction. In addition, the sample dispensing arm 118 has initial positions in a rotational direction and an up-and-down direction and is provided with sensors (not shown). The sensors detect that the sample dispensing arm 118 is returned to the initial positions. When receiving an instruction for measurement start and receiving an instruction for measurement restart after abort of the measurement operations by an error, the measurement control section 100 returns the sample dispensing arm 118 to the initial positions in the rotational direction and the up-and-down direction and then controls the sample dispensing arm 118 so as to perform a predetermined measurement operation.

The sample dispensing arm 118 has a function of suctioning the sample in a test tube 254 placed on a sample rack 253 and ejecting the suctioned sample to the cuvette held in the predetermined holding hole 109a on the rotation table section 109b of the first reaction section 109.

The reagent R2 dispensing arm 119 is provided with an arm section 119a and a shaft 119b.

A nozzle for suctioning and ejecting the reagent is attached to a tip end of the arm section 119a and is configured so as to be rotated around the shaft 119b and be moved in an up-and-down direction. In addition, the reagent R2 dispensing arm 119 has initial positions in a rotational direction and an up-and-down direction and is provided with sensors (not shown). The sensors detect that the reagent R2 dispensing arm 119 is returned to the initial positions. When receiving an instruction for measurement start and receiving an instruction for measurement restart after abort of the measurement operations by an error, the measurement control section 100 returns the reagent R2 dispensing arm 119 to the initial positions in the rotational direction and the up-and-down direction and then controls the reagent R2 dispensing arm 119 so as to perform a predetermined measurement operation.

The reagent R2 dispensing arm 119 has a function of suctioning the reagent R2 in the reagent container mounted on the reagent R2 mounting section 116 and ejecting the suctioned reagent R2 to the cuvette held in the predetermined holding hole 109a on the rotation table section 109b of the first reaction section 109.

The reagent R3 dispensing arm 120 is provided with an arm section 120a and a shaft 120b.

A nozzle for suctioning and ejecting the reagent is attached to a tip end of the arm section 120a and is configured so as to be rotated around the shaft 120b and be moved in an up-and-down direction. In addition, the reagent R3 dispensing arm 120 has initial positions in a rotational direction and an up-and-down direction and is provided with sensors (not shown). The sensors detect that the reagent R3 dispensing arm 120 is returned to the initial positions. When receiving an instruction for measurement start and receiving an instruction for measurement restart after abort of the measurement operations by an error, the measurement control section 100 returns the reagent R3 dispensing arm 120 to the initial positions in the rotational direction and the up-and-down direction and then controls the reagent R3 dispensing arm 120 so as to perform a predetermined measurement operation.

The reagent R3 dispensing arm 120 has a function of suctioning the reagent R3 in the reagent container mounted on the reagent R1/R3 mounting section 115 and ejecting the suctioned reagent R3 to the cuvette held in the predetermined holding hole 101a on the rotation table section 101b of the second reaction section 101.

The reagent R4 supply section 121 and the reagent R5 supply section 122 are provided to supply the reagent R4 and the reagent R5 to the cuvettes held in the predetermined holding holes 101a on the rotation table section 101b of the second reaction section 101, respectively.

The transporting section 250 has a right tank section 251 for setting the sample rack 253 holding a plurality of the test tubes 254 and a left tank section 252 for storing the sample rack 253 in which suction for the held test tubes 254 is completed.

The bar-code reader 255 is configured so as to read a sample rack bar-code of the sample rack 253 fed from the right tank section 251 of the transporting section 250 and test tube bar-codes of the test tubes 254 held in the sample rack.

Control Device

Figure 5:
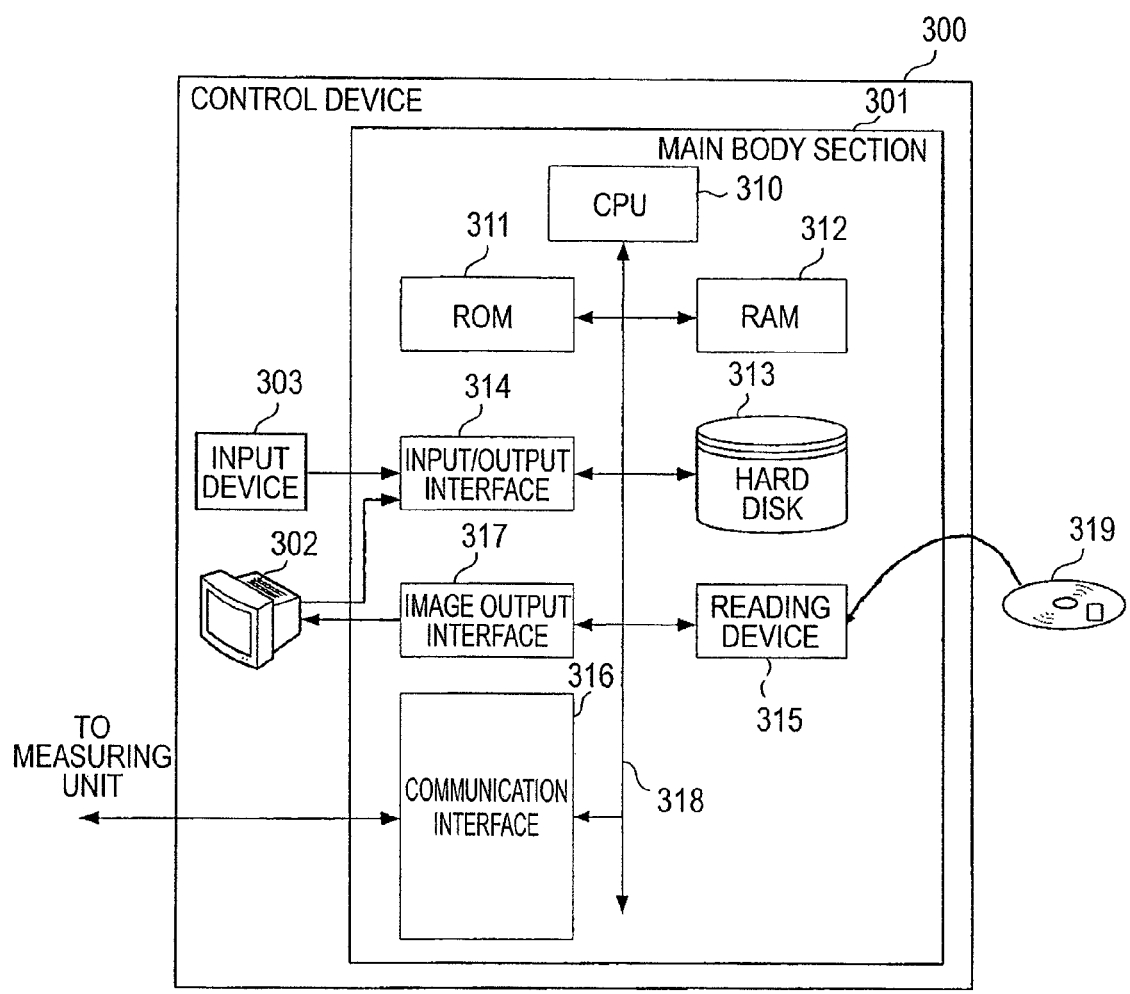
FIG. 5 is a hardware configuration diagram of a control device illustrated in FIG. 1.

FIG. 5 illustrates a block diagram of the control device 300. As illustrated in FIG. 5, the control device 300 is a computer mainly configured by a main body section 301, a display 302 and an input device 303.

The main body section 301 is mainly configured by a CPU 310, a ROM 311, a RAM 312, a hard disk 313, an input/output interface 314, a reading device 315, a communication interface 316 and an image output interface 317. The CPU 310, ROM 311, RAM 312, hard disk 313, input/output interface 314, reading device 315, communication interface 316 and image output interface 317 are connected to each other by a bus 318 such that data communication can be mutually performed.

The CPU 310 can execute computer programs stored in the ROM 311 and the hard disk 313 and a computer program loaded to the RAM 312. By executing an application program on the CUP 310, the functional blocks to be described later are realized and the computer functions as the control device 300.

The ROM 311 includes a mask ROM, a PROM, an EPROM and an EEPROM and a computer program to be executed on the CPU 310 and data to be used for the computer program are recorded therein.

The RAM 312 includes a SRAM and a DRAM. The RAM 312 is used to read computer programs recorded in the ROM 311 and the hard disk 313. Moreover, the RAM 312 is used as a work area of the CPU 310 when the computer programs are executed.

On the hard disk 313, various computer programs for being executed on the CPU 310, such as an operating system and an application program, and data to be used for the computer programs are installed.

The reading device 315 includes a flexible disk drive, a CD-ROM drive, and a DVD-ROM drive to read a computer program or data recorded in a portable recording medium 319.

The input/output interface 314 includes, for example, a serial interface such as USB, IEEE1394 and RS-232C, a parallel interface such as SCSI, IDE, and IEEE1284, and an analog interface including a D/A converter and an A/D converter. The input/output interface 314 is connected to the input device 303 including a keyboard, a mouse and a handy bar-code reader. An operator can input data to the main body 301 by using the input device 303.

The communication interface 316 is, for example, an Ethernet (registered trade name) interface. Through the communication interface 316, the control device 300 can send and receive data to and from the measurement control section 100 by using a predetermined communication protocol.

The image output interface 317 is connected to the display 302 including LCD and CRT to output a picture signal corresponding to image data given from the CPU 310 to the display 302.

Figure 9:
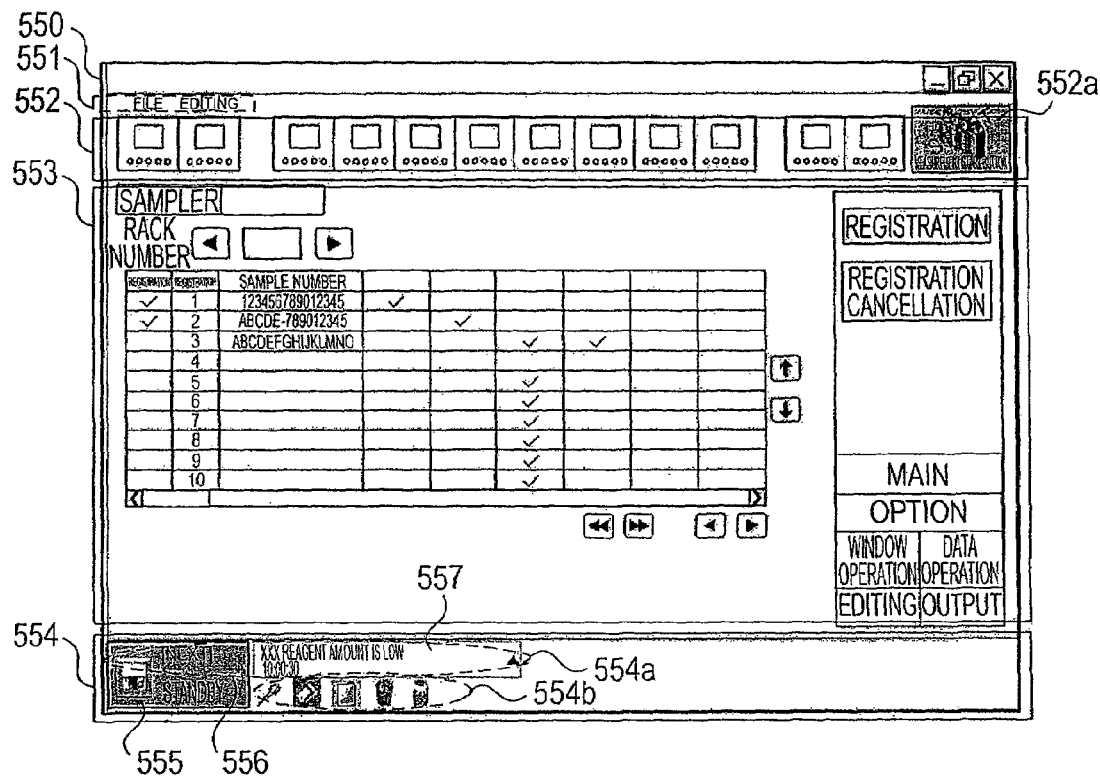
FIG. 9 is an example of an operation window where a user performs a measurement start operation.
Figure 10:
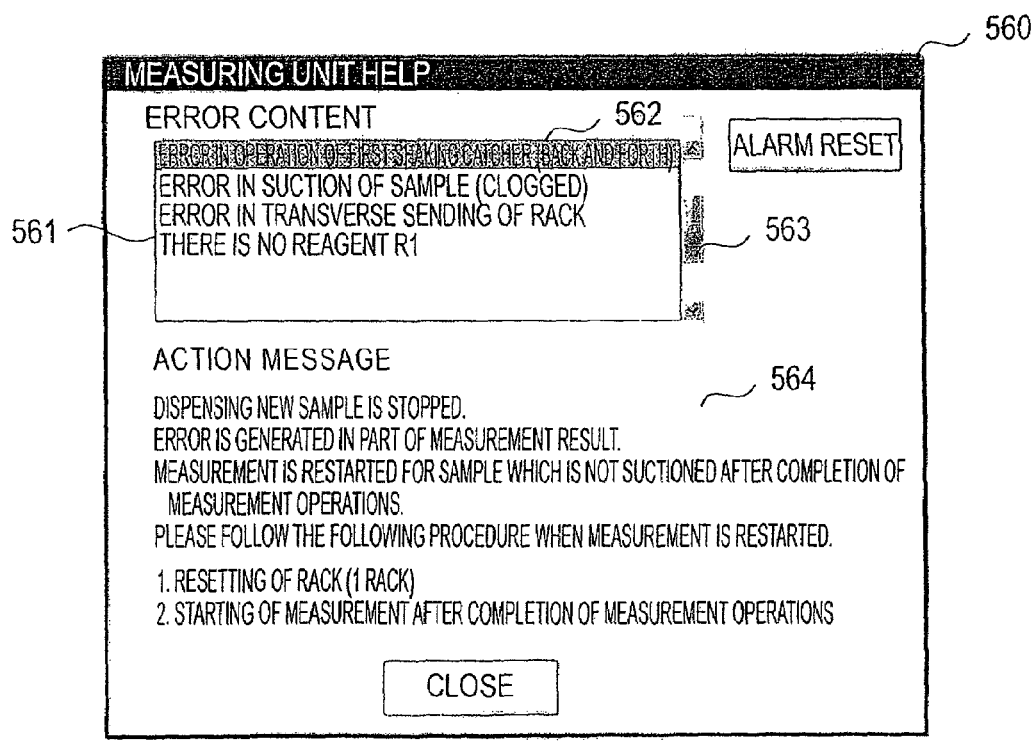
FIG. 10 is an example of a help window which is displayed on a display of the control device.

The display 302 displays an image (window) in accordance with the input picture signal. FIG. 9 is an example of an operation window 550 for operating the measuring unit 2, which is displayed on the display 302.

The operation window 550 has a menu bar 551, a tool bar 552, a function display area 553 and a status bar 554.

In the menu bar 551, route menus of the operation window 550a redisplayed. The route menus have submenus and pull-down menus can be displayed by an input operation of a mouse (not shown) or the keyboard 303.

In the tool bar 552, a plurality of tool button icons for executing functions which are frequently used in the operation window 550 are displayed, and a measurement start button 552a is displayed such that the user starts the measurement and restarts the measurement when an error occurs.

The function display area 553 is an area for displaying a measurement order input window, an accuracy management window and the like. The function display area 553 of FIG. 9 is an example of a window where a measurement order is input.

The status bar 554 has a device status indicator 554a and a consumable supply indicator 554b. The device status indicator 554a has a device status indicator 555, a device status message 556 and an error message 557. The device status indicator 555 indicates to the user the status of the measuring unit 2 by a background color and the background color is changed in accordance with the status of the measuring unit 2. For example, the background color is changed to a green color when the measuring unit is in a standby status, changed to an orange color when the measuring unit is in an under measurement status, and changed to a red color when an error is generated. The device status message 556 displays a message to indicate the status of the measuring unit 2. For example, the device status message shows "standby" when the measuring unit is in a standby status, shows "under measurement" when the measuring unit is in an under measurement status, and shows "error" when an error is generated. The error message 557 displays the content of the error generated in the measuring unit 2.

The consumable supply indicator 554b is an area for displaying the availabilities of the pipette tips, cuvettes and reagents as consumable supplies in the device.

Overall Process

Hereinafter, a process flow of the immunological analyzer 1 will be described using FIGS. 6 to 11.

Figure 6:
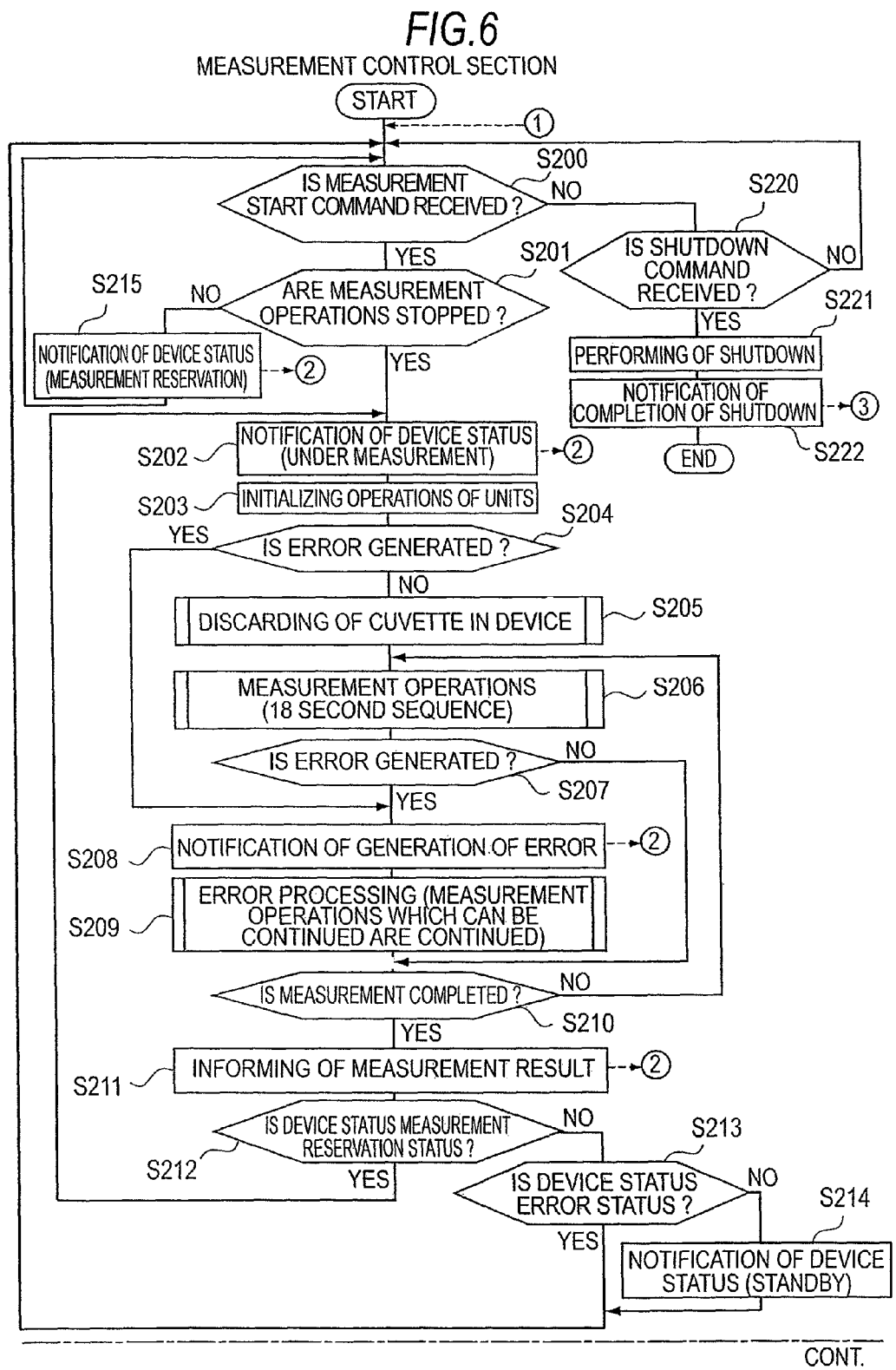
FIG. 6 is an example of a flowchart illustrating a main process which is performed by the analyzer.

FIG. 6 is a flowchart illustrating a main process of the immunological analyzer 1. The control device 300 determines whether the user presses the measurement start button 552a (Step S100) illustrated in FIG. 9, which is displayed on the display 302 of the control device 300, or a shutdown button (not shown) (Step S140). When the user presses the measurement start button 552a (Yes in Step S100), the control device 300 transmits a measurement start command to the measurement control section 100 (Step S101).

Figure 8:
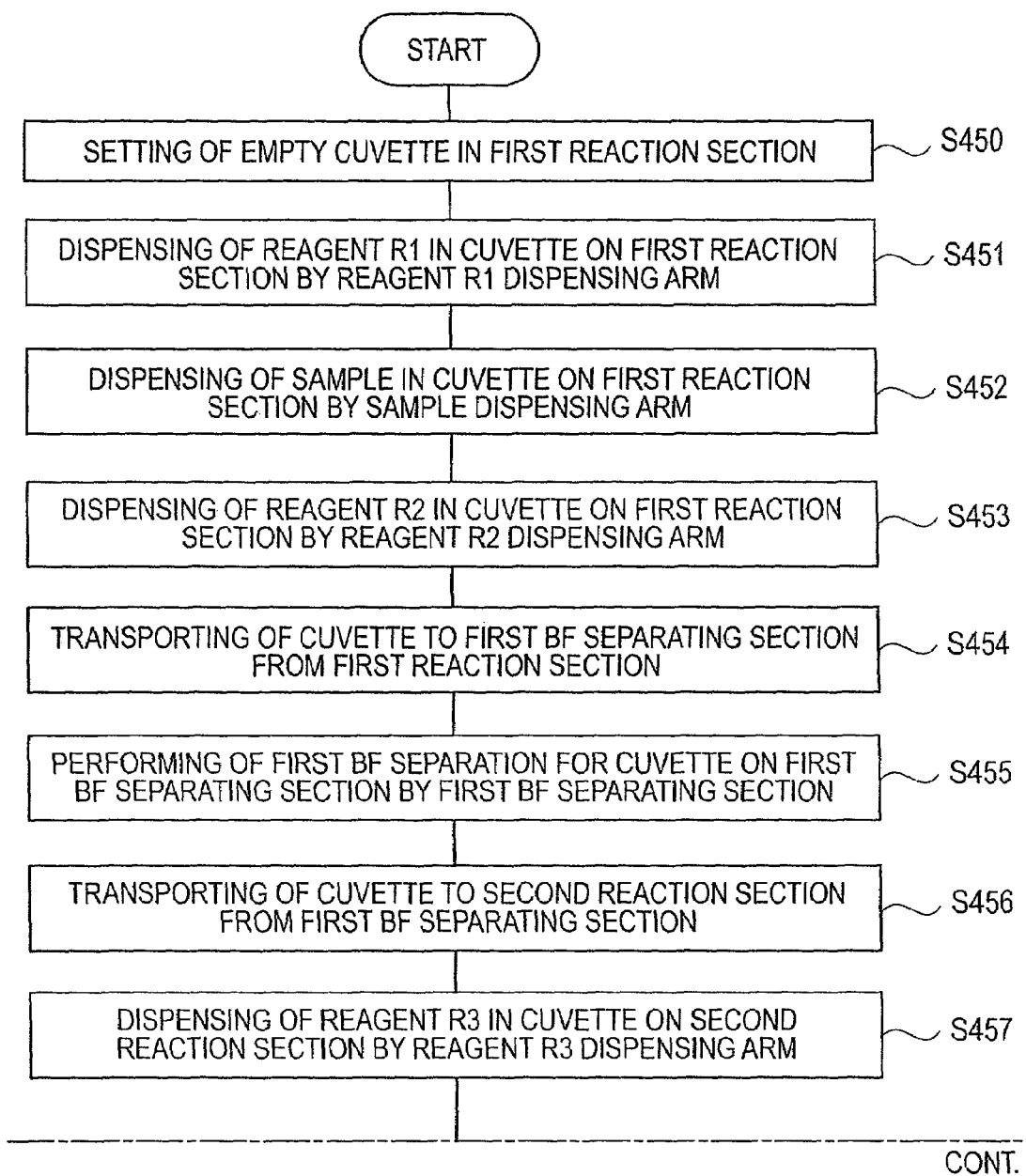
FIG. 8 is a diagram illustrating a flow of measurement operations of the immunological analyzer illustrated in FIG. 1.
Figure 8:
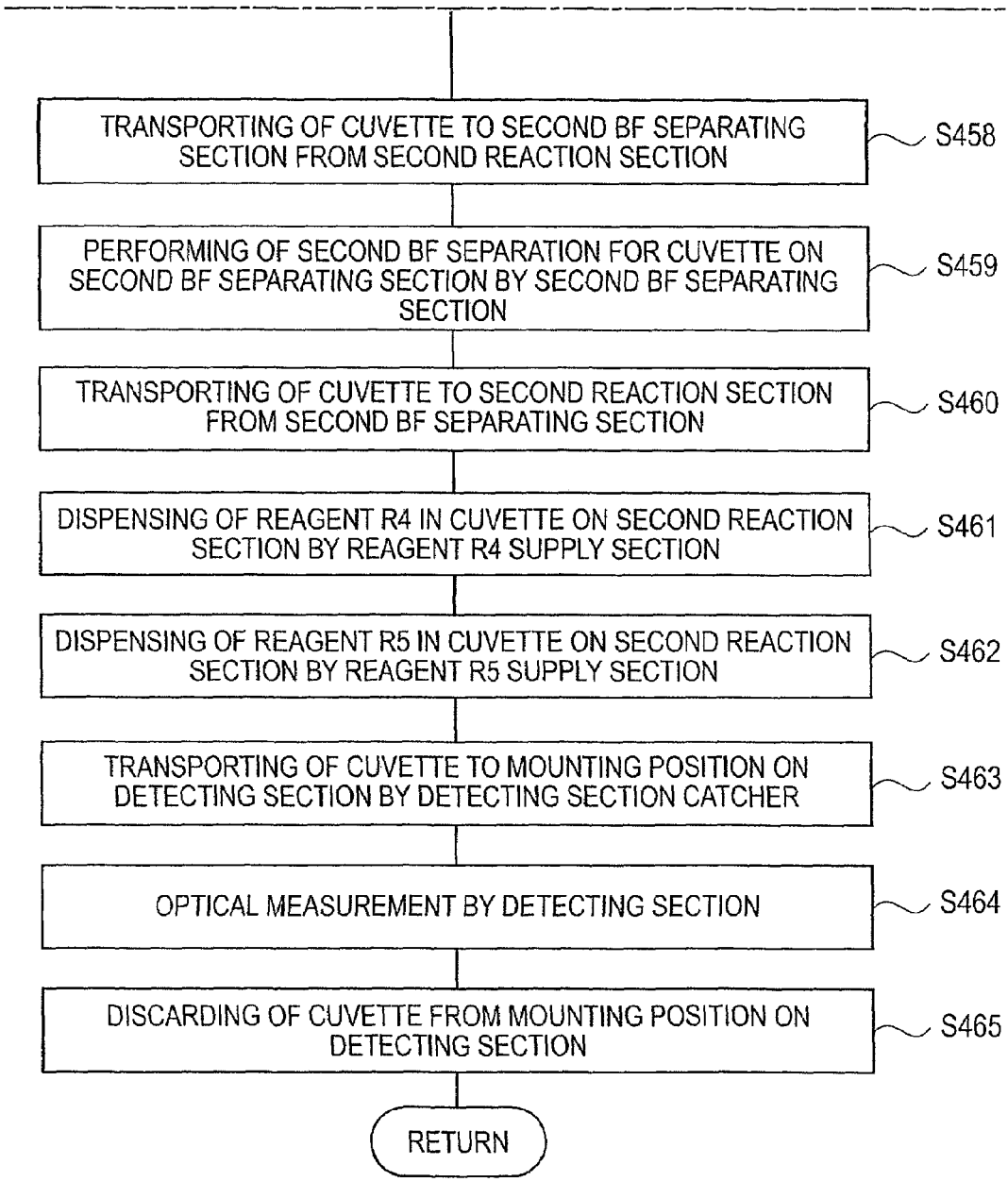

The measurement control section 100 waits to receive the measurement start command or a shutdown command from the control device 300 (Step S200 or Step S220). When the measurement control section receives the measurement start command (Yes in Step S200), determining whether the measuring unit 2 stops the measurement operations to be described later in FIG. 8 is performed (Step S201). When the measurement operations are stopped (Yes in Step S201), the measurement control section 100 notifies the control device 300 of that the device status is changed to an under measurement status (Step S202), and initializing operations for moving the units such as the rotation table section 101b of the second reaction section 101, the rotation table section 109b of the first reaction section 109, the reagent R1 dispensing arm 117, the sample dispensing arm 118, the reagent R2 dispensing arm 119, the reagent R3 dispensing arm 120, the second shaking catcher 102 and the first shaking catcher 110 and the like to their initial positions are performed (Step S203).

The initializing operations are performed to prevent the units to interfere with another unit when the measurement is restarted. That is, when the measurement operations are completed, the measurement control section 100 performs the initializing operations for the units, but after completion of the measurement, the user may touch the units by hand and the units may be displaced from their initial positions. In this state, when the user restart the measurement, the units may move to positions distant from predetermined positions and may interfere with another unit. Accordingly, when the measurement start command is received from the control device 300 (Yes in Step S200), the measurement control section 100 necessarily performs the initializing operations for the units (Step S203).

When it is determined that the measurement operations are not stopped (No in Step S201), the measurement control section 100 notifies the control device 300 of that the device status is changed to a measurement reservation status (Step S215). The measurement reservation status as the device status represents a status in which the user presses the measurement start button 552a to restart the measurement when an error is generated in the measuring unit 2 and the measurement operations are continued for the cuvette on which the measurement operations can be continued.

In addition, the measurement control section 100 determines whether an error is generated during the initializing operations for the units (Step S203) (Step S204). When the error is not generated during the initializing operations (No in Step S204), the measurement control section 100 performs a cuvette discarding process to be described later (Step S205) to discard the cuvette remaining on the measuring unit 2.

In this embodiment, the measurement operations for the cuvette proceed by transporting a plurality of the units. However, despite normal completion of the measurement, there is a possibility that the measurement is completed while the cuvette remains on the immunological analyzer 1 because of an error in detection of the sensor. In this state, when the user restarts the measurement, the cuvette remaining on the immunological analyzer 1 may interfere with a cuvette which is newly set on the immunological analyzer 1 for the measurement. Accordingly, it is confirmed whether the cuvette remains on the immunological analyzer 1 before the measurement operations are started, and it is necessary to discard the cuvette when the cuvette remains.

In case where the error is generated during the initializing operations for the units (Step S203) (Yes in Step S204), for example, in case where the reagent R1 dispensing arm 117 is moved to the initial positions in the rotational direction and the up-and-down direction but cannot be returned to the initial position in the rotational direction by an obstacle obstructing the rotation operation, the process proceeds to Step S208.

Figure 7:
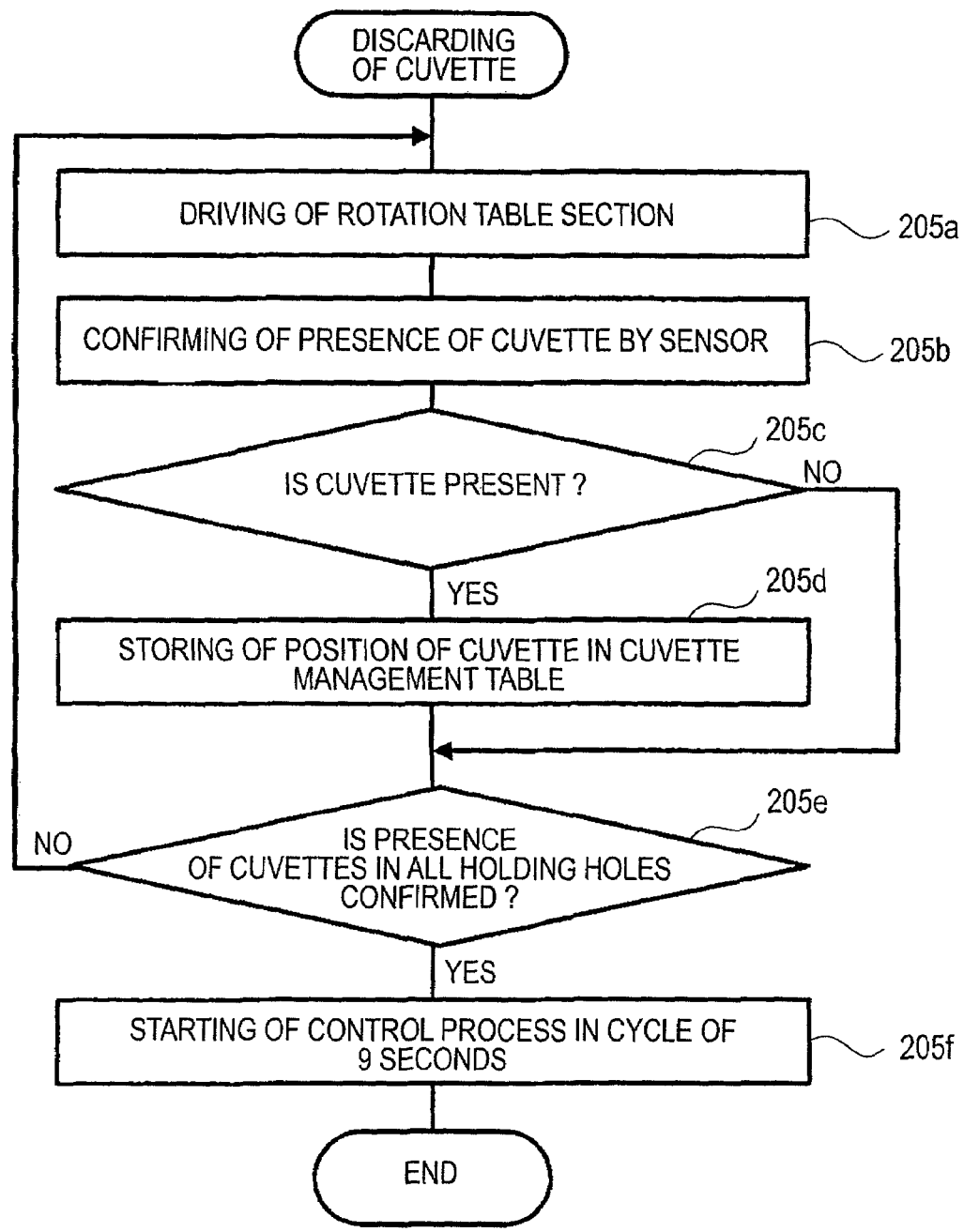
FIG. 7 is an example of a flowchart illustrating a cuvette discarding process which is performed by the measurement control section.

Herein, a flow of the cuvette discarding process (Step S205) will be described using FIG. 7.

The measurement control section 100 controls the motor to rotate the rotation table section 109b of the first reaction section 109 and the rotation table section 101b of the second reaction section 101 by predetermined angles (Step S205a), and detect whether the cuvette is present in the holding holes of the first reaction section 109 and the second reaction section 101 on the basis of the outputs of the sensor 109c on the first reaction section 109 and the sensor 101c on the second reaction section 101 (Step S205b). When the measurement control section 100 determines that the cuvette is present on at least one of the rotation table section 109b of the first reaction section 109 and the rotation table section 101b of the second reaction section 101 (Yes in Step S205c), the measurement control section 100 stores the position of the cuvette on the measuring unit 2 (Step S205d). In this embodiment, the first BF separating section 107 and the second BF separating section 106 are not provided with sensors for detecting the cuvette and it is regarded that all of the holding sections of the first BF separating section 107 and the second BF separating section 106 have the cuvettes present therein. When it is determined that the cuvette is not present (No in Step S205c), the process proceeds to Step S205e.

When confirmation for confirming whether the cuvette is present on all of the holding holes of the rotation table section 109b of the first reaction section 109, the first BF separating section 107, the rotation table section 101b of the second reaction section 101 and the second BF separating section 106 is completed (Yes in Step S205e), the measurement control section 100 starts a control process having a cycle of 9 seconds to be described later (Step S205f) and performs discarding of all of the cuvettes held in the holding holes of the rotation table section 109b of the first reaction section 109, the first BF separating section 107, the rotation table section 101b of the second reaction section 101 and the second BF separating section 106.

When the confirmation for confirming whether the cuvette is present on all of the holding holes of the rotation table section 109b of the first reaction section 109, the first BF separating section 107, the rotation table section 101b of the second reaction section 101 and the second BF separating section 106 is not completed (No in Step S205e), the process returns to Step S205a.

Herein, the control process having a cycle of 9 seconds (Step S205f) is a process of controlling the units by the measurement control section 100 so as to perform predetermined operations in a cycle of 9 seconds when the discarding of the cuvette is performed and of discarding the cuvette on the measuring unit 2. For example, the rotation table section 101b of the second reaction section 101 is rotated by a predetermined angle by the motor 101d in a cycle of 9 seconds and the units performs the predetermined operations until the rotation table section 101b is rotated next time by a predetermined angle. In addition, when the measurement operations are performed, the measurement control section 100 controls the units such that the units perform the predetermined operations in a cycle of 18 seconds.

Since the number of the units to be operated at the time of the discarding of the cuvette is smaller than the number of the units to be operated at the time of the measurement operations, the units have a smaller number of waiting times for waiting completion of a predetermined operation of another unit in order to avoid interference and thus the cycle of controlling a plurality of the units can be shortened.

For example, at the time of the measurement operations, the reagent R1 dispensing arm 117 and the reagent R3 dispensing arm 120 access the reagent R1/R3 mounting section 115 to suction the reagents. The reagent R1/R3 mounting section 115 has a configuration in which a plurality of reagent R1/R3 bottles containing the reagent R1 and the reagent R3 in sets can be mounted. When the reagent R1 dispensing arm 117 and the reagent R3 dispensing arm 120 access the reagent R1/R3 mounting section 115 for the suction, the measurement control section 100 moves a corresponding reagent R1/R3 bottle to a position which is accessed by the reagent dispensing arm.

However, the reagents R1 and R3 are mounted in the reagent R1/R3 mounting section 115 in sets and the reagents accessed by the reagent dispensing arms accessing the reagent R1/R3 mounting section 115 for the suction are independent from each other. Accordingly, after completion of a suction operation of the reagent R1 dispensing arm 117, the reagent R3 dispensing arm 120 should wait for the reagent R1/R3 bottle to be moved in a suction position for the reagent R3 and then start a suction operation.

At the time of the discarding of the cuvette, thanks to the units not required to perform the predetermined operations such as the suction operations of the reagent R1 dispensing arm 117 and the reagent R3 dispensing arm 120, the cycle of operating a plurality of the units can be reduced more than the cycle for the measurement operations.

Returning to FIG. 6, after completion of the discard process of the cuvette in the device (Step S205), the measurement control section 100 performs the measurement operations (Step S206).

In this embodiment, the measurement control section 100 controls the units in a cycle of 18 seconds and performs the measurement operations. A flow of the measurement operations will be described using a flowchart illustrated in FIG. 8. First, the measurement control section 100 controls the first shaking catcher 110 to transport the cuvette to the holding hole 109a positioned at the position 150 on the rotation table section 109b of the first reaction section 109 from the cuvette supply device 111 and to set the cuvette (Step S450). The measurement control section 100 detects that the cuvette is transported to the holding hole 109a positioned at the position 150 on the rotation table section 109b by the output of the sensor 109c.

Next, the measurement control section 100 controls the reagent R1 dispensing arm 117 to suction the reagent R1 in the reagent container mounted on the reagent R1/R3 mounting section 115 by the nozzle section and turns the arm 117a to the first reaction section 109 to eject the suctioned reagent R1 into the cuvette held in the holding hole 109a of the rotation table section 109b (Step S451). The reagent R1 includes the capture antibodies bound to the antigens included in the sample.

Next, the measurement control section 100 controls the sample dispensing arm 118 to mount a pipette tip transported by the tip transporting section 112 and to suction the sample such as blood from the test tube 254 placed on the sample rack 253 transported to the suction position by the transporting section 250. Then, the measurement control section 100 turns the arm section 118a of the sample dispensing arm 118 to the first reaction section 109 to eject the suctioned sample into the cuvette in which the reagent R1 is dispensed in the reagent R1 dispensing step (Step S452).

After that, the measurement control section 100 shakes the cuvette containing the reagent R1 and the sample by the first shaking catcher 110. The shaken reagent R1 and sample are incubated in the cuvette in the holding hole 109a on the rotation table section 109b for predetermined time. As a result, the capture antibodies (reagent R1) and the antigens in the samples are bound to each other.

Next, the measurement control section 100 controls the reagent R2 dispensing arm 119 to suction the reagent R2 in the reagent container mounted on the reagent R2 mounting section 116 by the nozzle section and turns the arm 119a to the first reaction section 109 to eject the suctioned reagent R2 into the cuvette containing the reagent R1 and the sample incubated for the predetermined time (Step S453). The reagent R2 includes the magnetic particles to be bound to the capture antibodies bound to the antigens included in the sample.

After that, the measurement control section 100 controls the first shaking catcher 110 to shake the cuvette containing the reagent R1, the sample and the reagent R2. The shaken reagent R1, sample and reagent R2 are incubated in the cuvette in the holding hole 109a of the first reaction section 109 for predetermined time. As a result, the magnetic particles (reagent R2) and the capture antibodies (reagent R1) bound to the antigens in the sample are bound to each other.

Next, the measurement control section 100 controls the first shaking catcher 110 to transport the cuvette containing the incubated reagent R1, sample and reagent R2 to the position 186 on the first BF separating section 107 from the holding hole 109a positioned at the position 165 (Step S454).

Next, the magnetic particles in the cuvette held on the first BF separating section 107 are collected by a magnet disposed on the side of the cuvette. The measurement control section 100 inserts the nozzle section of the first BF separating section 107 into the cuvette to suction the specimen. In this manner, unnecessary components are removed except for the magnetic particles and the antigens bound to the magnetic particles via the capture antibodies (Step S455).

In order to more securely remove the unnecessary components, the measurement control section 100 supplies a cleaning liquid to the cuvette and shakes the cuvette. Then, an operation of removing the unnecessary components with the cleaning liquid by the nozzle section is repeatedly performed. The measurement control section 100 rotates the first BF separating section 107 to transport the cuvette in which the unnecessary components are removed to a position where the cuvette can be grasped by a transporting mechanism 138.

Next, as illustrated in FIG. 1, the cuvette in which the unnecessary components are removed by the first BF separating section is grasped by the arm section 108a of the transporting mechanism 108 and then is transported to the holding hole 101a positioned at the position 192 on the rotation table section 101b of the second reaction section 101 (Step S456). The measurement control section 100 detect that the cuvette is transported to the holding hole 101a at the position 192 on the rotation table section 101b by the output of the sensor 101c.

Next, the measurement control section 100 controls the reagent R3 dispensing arm 120 to suction the reagent R3 in the reagent container mounted on the reagent R1/R3 mounting section 115 by the nozzle section and turns the arm 120a to the second reaction section 101 to eject a predetermined amount of the reagent R3 into the cuvette containing the magnetic particles (reagent R2) and the antigens in the sample bound to each other via the capture antibodies (reagent R1) (Step S457). The reagent R3 includes the labeled antibodies to be bound to the antigens in the sample.

Then, the measurement control section 100 controls the second shaking catcher 102 to shake the cuvette containing the capture antibodies (reagent R1), the antigens (sample), the magnetic particles (reagent R2) and the reagent R3 including the labeled antibodies. The shaken capture antibodies (reagent R1), antigens (sample), magnetic particles (reagent R2) and reagent R3 including the labeled antibodies are incubated in the cuvette in the holding hole 101a of the second reaction section 101 for predetermined time. As a result, the antigens bound to the magnetic particles (reagent R2) via the capture antibodies (reagent R1) and the labeled antibodies (reagent R3) are bound to each other.

Next, the measurement control section 100 controls the second shaking catcher 102 to transport the cuvette containing the incubated capture antibodies (reagent R1), antigens (sample), magnetic particles (reagent R2) and reagent R3 including the labeled antibodies to the position 228 on the second BF separating section 106 from the holding hole 101a positioned at the position 202 on the rotation table section 101b (Step S458).

Next, as in the step performed on the first BF separating section 107, the magnetic particles in the cuvette held on the second BF separating section 106 are collected by a magnet disposed on the side of the cuvette. The measurement control section 100 inserts the nozzle section of the second BF separating section 106 into the cuvette to suction the specimen. In this manner, unnecessary components are removed except for the magnetic particles and the antigens bound to the magnetic particles via the capture antibodies (Step S459). In order to more securely remove the unnecessary components, the measurement control section 100 supplies a cleaning liquid to the cuvette and shakes the cuvette. Then, an operation of removing the unnecessary components with the cleaning liquid by the nozzle section is repeatedly performed.

Then, the measurement control section 100 rotates the second BF separating section 106 to transport the cuvette containing the specimen in which the unnecessary components are removed and which includes the antigens bound to the labeled antibodies to the position 233 where the cuvette can be transported by the second shaking catcher 102.

Next, the measurement control section 100 controls the second shaking catcher 102 to transport the cuvette in which the unnecessary components are removed to the holding hole 101a positioned at the position 207 on the rotation table section 101b of the second reaction section 101 again (Step S460).

Next, the measurement control section 100 controls the reagent R4 supply section 121 to eject the reagent R4 (dispersion liquid) in the reagent container (not shown) mounted below the measuring unit 2 into the cuvette containing the capture antibodies (reagent R1), the magnetic particles (reagent R2), the labeled antibodies (reagent R3) and the antigens in the sample from the nozzle section (Step S461).

Next, the measurement control section 100 controls the reagent R5 supply section 122 to eject the reagent R5 in the reagent container (not shown) mounted below the measuring unit 2 into the cuvette containing the capture antibodies (reagent R1), the magnetic particles (reagent R2), the labeled antibodies (reagent R3), the dispersion liquid (reagent R4) and the antigens in the sample from the nozzle section (Step S462). The reagent R5 includes the luminescent substrates which emit light by being reacted with the labeled antibodies of the reagent R3.

The measurement control section 100 controls the second shaking catcher 102 to shake the cuvette containing the capture antibodies (reagent R1), the antigens (sample), the magnetic particles (reagent R2), the labeled antibodies (reagent R3), the dispersion liquid (reagent R4) and the reagent R5 including the luminescent substrates and incubate them in the cuvette for predetermined time.

Then, the measurement control section 100 controls the detecting section catcher 104 to transport the cuvette containing the incubated capture antibodies (reagent R1), antigens (sample), magnetic particles (reagent R2), labeled antibodies (reagent R3), dispersion liquid (reagent R4) and reagent R5 including the luminescent substrates to the mounting position 103a (Step S463). An amount of luminescence generated in the course of the reaction of the labeled antibodies of the reagent R3 with the luminescent substrates of the reagent R5 is acquired by a photo multiplier tube (Step S464). The acquired detection result is transmitted to the control device 300 in Step S212 of FIG. 6.

After the detection, the cuvette at the mounting position 103a of the detecting section 103 is discarded to the discarding bag 105b disposed below the measuring unit 2, illustrated in FIG. 3, through the hole of the discarding member 105a by the detecting section catcher 104 (Step S465).

Returning to FIG. 6, the measurement control section 100 determines whether an error is generated in the measuring unit 2 during the measurement operations (Step S206) (Step S207). When the error is generated in the measuring section 2 during the measurement operations (Yes in Step S207), the measurement control section 100 notifies the control device 300 of that the error is generated (Step S208).

Next, the measurement control section 100 performs an error processing (Step S209) to be described later. For the cuvette satisfying the conditions for continuing the measurement operations, the measurement operations are continued, and after analysis of the cuvette on which the measurement operations are continued is completed, the measurement operations are stopped.

Figure 11:
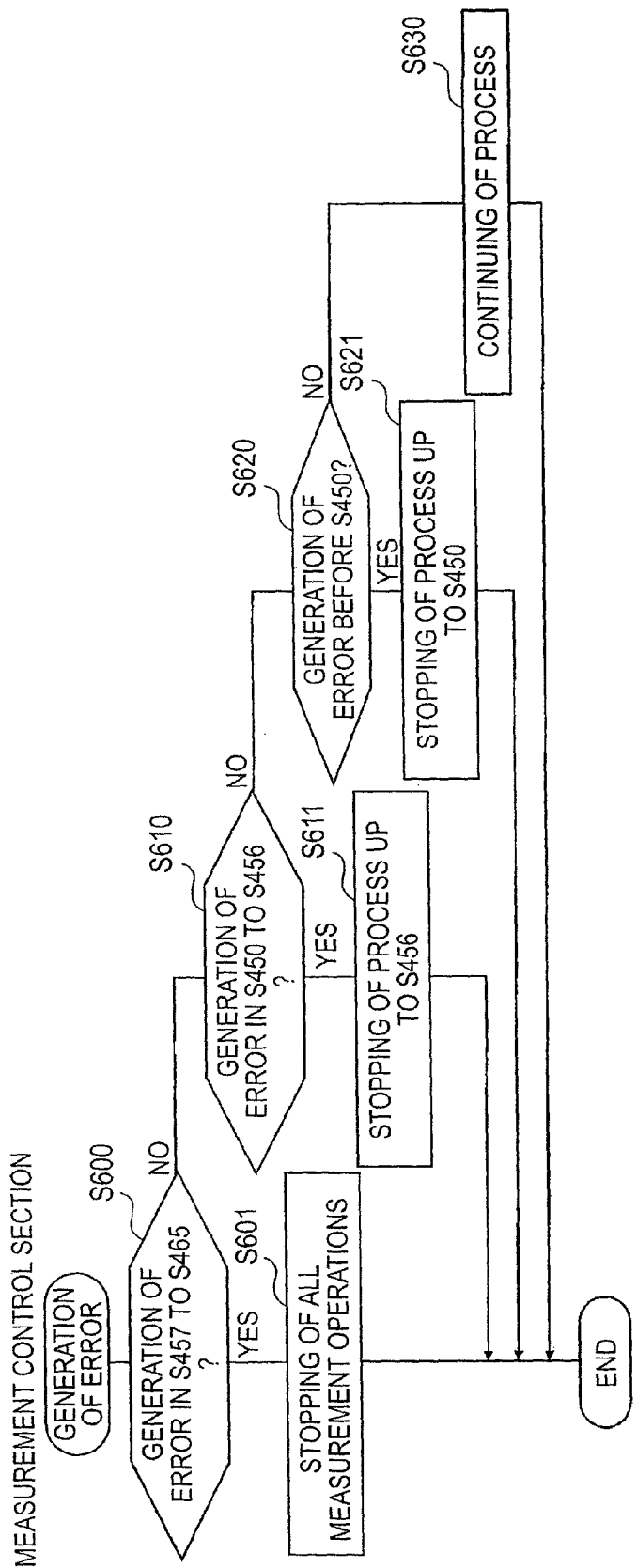
FIG. 11 is an example of a flowchart illustrating an error processing which is performed by the measurement control section after the generation of an error.

Using the flowchart illustrated in FIG. 11, the error processing (Step S209) will be described which is performed by the measurement control section 100 when it is determined that the error is generated in the measuring unit 2 during the measurement operations (Yes in Step S207).

When the error is detected in Step S207 illustrated in FIG. 6, the measurement control section 100 determines whether the measurement operations are continued depending on the step in which the error is generated. When the error is generated in Steps S457 to S465 illustrated in FIG. 8 (Yes in Step S600), the measurement control section 100 stops all of the measurement operations (Step S601).

When the error is detected in Steps S450 to S456 illustrated in FIG. 8 (No in Step S600 and Yes in Step S610), the measurement control section 100 stops the process up to Step S456 illustrated in FIG. 8 and continues the process from Step S457 (Step S611).

When the error is generated before Step S450 illustrated in FIG. 8 (No in Step S600, No in Step S610 and Yes in Step S620), the measurement control section 100 stops the process up to Step S450, that is, stops a new sample being suctioned by the sample dispensing arm 118 and continues the process from Step S450 (Step S621).

When an error causing a warning to be issued to the user, such as expired reagents, is generated (No in Step S600, No in Step S610 and No in Step S620), the measurement control section 100 displays the generation of the error on a help window 560 and continues the measurement operations (Step S630).

Returning to FIG. 6, when the measurement for the cuvette on which the measurement operations are continued is completed (Yes in Step S210), the measurement control section 100 notifies the control device 300 of the measurement result (Step S211). When the cuvette on which the measurement operations is continued is present in the measuring unit 2 (No in Step S210), the process returns to Step S206.

The measurement control section 100 notifies the control device 300 of the measurement result and then determines a current device status (Step S212). When the device status is a measurement reservation status (Yes in Step S212), the measurement control section 100 allows the process to proceed to Step S202 and notifies the control device 300 of that the device status is changed to an under measurement status (Step S202). Then, the measurement control section performs the initializing operations for the units (Step S203). After the discard process of the cuvette in the device is completed (Step S205), the measurement operations are performed (Step S206).

When the device status is an error status (No in Step S212, Yes in Step S213), the measurement control section 100 allows the process to return to Step S200 and waits for the measurement start command for restarting the measurement from the control device 300 (Step S200).

When the device status is not the measurement reservation status or the error status, that is, is in the under measurement status (No in Step S212 and No in Step S213), the measurement control section 100 notifies the control device 300 of that the device status is changed to the standby status (Step S214). Then, the measurement control section 100 allows the process to return to Step S200 and waits for the measurement start command for staring the measurement from the control device 300 (Step S200).

The control device 300 waits to receive the device status (Step S102), the notification of the generation of the error (Step S120) or the measurement result (Step S130) from the measurement control section 100. When receiving the device status (Yes in Step S102), the control device allows the process to proceed to Step S103. When the content of the device status received from the measurement control section 100 is an under measurement status (Yes in Step S103), the control device 300 changes the background color of the device status indicator 554a illustrated in FIG. 9 to an orange color, changes the device status message 556 to "under measurement" (Step S104), erases all of the error messages displayed in an error content display box 561 of the help window 560 of FIG. 10 to be described later (Step S105) and allows the process to return to Step S100.

When the device status received from the measurement control section 100 is a measurement reservation status (No in Step S103 and Yes in Step S106), the control device 300 changes the background color of the device status indicator 554a illustrated in FIG. 9 to an orange color, changes the device status message 556 to "measurement reservation" (Step S107) and allows the process to return to Step S100.

When the device status received from the measurement control section 100 is a standby status (No in Step S103, No in Step S106 and Yes in Step S108), the control device 300 changes the background color of the device status indicator 554a illustrated in FIG. 9 to a green color, changes the device status message 556 to "standby" (Step S109) and allows the process to return to Step S100.

When the device status received from the measurement control section 100 is not an under measurement status, a measurement reservation status and a standby status (No in Step S103, No in Step S106 and No in Step S108), the process returns to Step S100.

When the control device 300 receives the notification of the generation of the error from the measurement control section 100 (No in Step S102 and Yes in Step S120), the control device 300 notifies, through the display 302 or an alarm, the user of the immunological analyzer 1 of that the error is generated in the measuring unit 2 (Step S121). Next, the control device 300 displays the error generated in the measuring unit 2 and a method for error recovery on the help window 560 to be described later (Step S122) and allows the process to return to Step S100.

An example of the help window 560 showing the user the error generated in the measuring unit 2 and the method of error recovery. The help window 560 mainly has the error content display box 561, an error selecting cursor 562, a scroll bar 563 and an action message box 564.

In the error content display box 561, a plurality of errors can be displayed which are generated in the measuring unit 2 and the control device 300. In this embodiment, generated errors are displayed in a sequence of importance of the errors. However, the errors may be displayed in a sequence of generation of the errors. The error selecting cursor 562 is displayed on the error which is most recently generated in default. However, by operating a mouse, the error selecting cursor can be displayed on other errors displayed in the error content display box 561. When a plurality of errors are generated and the errors are not displayed in the error content display box 561 at one time, the scroll bar 563 is moved up and down to display in the error content display box 561 errors which are not displayed. The action message box 564 displays an action message corresponding to the error selected by the error selecting cursor 562.

Returning to FIG. 6, when the control device 300 receives the notification of the generation of the error from the measurement control section 100 (No in Step S102 and Yes in Step S120) and then the user presses the measurement start button 552a illustrated in FIG. 9 (Yes in Step S100), the measurement start command for restarting the measurement is transmitted to the measurement control section 100 (Step S101).

When receiving the measurement start command from the control device 300 (Yes in Step S200), the measurement control section 100 determines whether the measurement operations are stopped (Step S201). When the measurement operations are stopped (Yes in Step S201), the measurement control section 100 notifies the control device 300 of that the device status is changed to an under measurement status (Step S202) and performs the initializing operations for the units (Step S203). Most errors generated in the measuring unit 2 are caused because the unit interfering with another unit during the measurement operations cannot access a predetermined position, not because the unit is displaced or broken down. Accordingly, most errors generated in the measuring unit 2 can be recovered by performing the initializing operations for the units, not by adjusting the position of the unit or exchanging the unit.

When normally completing the initializing operations, the measurement control section 100 determines that the error generated in the measuring unit 2 is completely recovered. In this manner, for example, when a plurality of errors are generated in the measuring unit 2, the user has no need to select the generated errors one by one and perform the recovery operation in accordance with a recovery sequence and thus the measurement can be rapidly restarted. Next, the measurement control section 100 determines whether an error is generated during the initializing operations (Step S204). When the error is not generated during the initializing operations (No in Step S204), the measurement control section 100 performs a process of discarding the cuvette in the device (Step S205), and after completion of the process of discarding the cuvette, the measurement control section restarts the measurement operations (Step S206).

When the measurement operations are not stopped (No in Step S201), that is, when the measurement operations which can be continued by the error processing are continued after the generation of the error, the control device 300 is notified of that the device status is changed to a measurement reservation status (Step S215) and the process returns to Step S200. When the measurement (Step S209) continued by the error processing is completed (Yes in Step S210) during the time that the measurement control section waits to receive the measurement start command (Step S200) or the shutdown command (Step S220) from the control device 300, the measurement control section 100 informs the control device 300 of the measurement result (Step S211) and determines whether the device status is in a measurement reservation status (Step S212). In this case, since the device status is the measurement reservation status (Yes in Step S212), the measurement control section allows the process to proceed to Step S202, notifies the control device 300 of that the device status is changed to an under measurement status (Step S202) and performs the initializing operations for the units (Step S203). Next, the measurement control section 100 determines whether an error is generated during the initializing operations (Step S204). When the error is not generated during the initializing operations (No in Step S204), the measurement control section 100 performs a process of discarding the cuvette in the device (Step S205), and after completion of the process of discarding the cuvette, the measurement control section restarts the measurement operations (Step S206).

When the error cannot be recovered by the initializing operations, the immunological analyzer 1 is operated as follows when determining that the error is generated during the initializing operations (Yes in Step S204), the measurement control section 100 notifies the control device 300 of that the error is generated (Step S208) and performs the error processing (Step S209). When the initializing operations are performed, there is no cuvette on which the measurement is continued. Accordingly, the measurement control section 100 stops the measurement operations. Next, the measurement control section 100 determines whether the measurement for the cuvette on which the measurement operations are continued is completed (Step S210). In this case, since the measurement operations are stopped, the measurement control section 100 determines that the measurement operations are completed (Yes in Step S210), notifies the control device 300 of the measurement result (Step S211) and allows the process to return to Step S200.

When receiving the notification of the generation of the error from the measurement control section 100 (No in Step S102 and Yes in Step S120), the control device 300 informs the user of the immunological analyzer 1 of the error generated in the measuring unit 2 through the display 302 or an alarm (Step S121). Next, the control device 300 displays the error generated in the measuring unit 2 and a method for error recovery on the help window 560 to be described later (Step S122) and allows the process to return to Step S100.

The user of the immunological analyzer 1 selects from the help screen 560 the errors which cannot be recovered by the initializing operations one by one and presses a recovery button (not shown) to recover the errors.

When the control device 300 receives the measurement result from the measurement control section 100 (No in Step S102, No in Step S120 and Yes in Step S130), the control device 300 analyzes the measurement result (Step S131) and allows the process to return to Step S100.

In the control device 300, when the user of the immunological analyzer 1 presses a shutdown button (not shown) on the display 302 to perform shutdown (No in Step S100 and Yes in Step S140), the control device 300 transmits the shutdown command to the measurement control section 100 (Step S141) and waits a notification of the completion of shutdown from the measurement control section 100 (Step S142). When receiving the completion of shutdown from the measurement control section 100 (Yes in Step S142), the control device 300 cuts the communication with the measurement control section 100 (Step S143) and completes the process.

When the shutdown button is not pressed (No in Step S100 and No in Step S140), the control device 300 allows the process to return to Step S100.

When receiving the shutdown command (No in Step S200 and Yes in Step S220), the measurement control section 100 cleans the reagent arm 115, a flow path (not shown) for dispensing the reagent and the like (Step S221) and transmits the completion of shutdown to the control device 300 (Step S222) after the shutdown is completed.

By the above-described processes, the user may only press the measurement start button to restart the measurement when an error is generated in the measuring unit 2. Accordingly, the measurement can be easily restarted. In addition, when performing the process of discarding the cuvette, the measurement control section 100 controls the plurality of units in a cycle shorter than a cycle of controlling the plurality of units during the measurement operations. Accordingly, the user can rapidly restart the measurement.

In this embodiment, the measurement start button is displayed on the display 302 of the control device 300. However, a switch for starting the measurement may be provided in the measuring unit 2.

In this embodiment, by using the sensor 109c on the first reaction section 109 and the sensor 101c on the second reaction section 101, the positions of the cuvettes present in the holding holes on the rotation table sections 109b and 101b are detected. However, it may be considered that all of the holding holes of the rotation table sections 109b and 101b have the cuvette present therein and thus the discard operation may be performed with no use of the sensors 109c and 101c.

In this embodiment, when the cuvettes are discarded, it is regarded that all of the holding sections of the first BF separating section 107 and the second BF separating section 106 have the cuvettes present therein. However, a sensor may be provided to detect whether the cuvette is present in the holding sections of the first BF separating section 107 and the second BF separating section 106.

In this embodiment, the first reaction section 109, the second reaction section 101, the first BF separating section 107 and the second BF separating section 106 are provided as units for holding the cuvette and transporting the cuvette at a predetermined speed. However, as disclosed in JP-A-6-82461, the measurement operations of the first reaction section 109, the second reaction section 101, the first BF separating section 107 and the second BF separating section 106 may be performed by one turntable.

In this embodiment, the cycle for the measurement is different from the cycle of discarding the cuvette. However, the cycle for the measurement may be the same as the cycle of discarding the cuvette.

In this embodiment, the cycle for the measurement is 18 seconds and the cycle of discarding the cuvette is 9 seconds. However, such a correspondence relation of the invention and this embodiment is one example and is not limited thereto.

What is claimed is:

1. An analyzer comprising:
    a specimen preparing section for preparing a measuring specimen including a specimen and a reagent, the specimen preparing section including a plurality of units performing predetermined operations;
    a detecting section for detecting a predetermined component from the measuring specimen prepared by the specimen preparing section;
    a start command receiver for receiving an instruction for starting measurement operations including preparing the measuring specimen by the specimen preparing section and detecting the predetermined component of the measuring specimen by the detecting section;
    a measurement controller for controlling the plurality of units and the detecting section so as to perform the measurement operations when the start command receiver receives the instruction for starting the measurement operations;
    an error detecting section for detecting an error in the operations of the plurality of units;
    a measurement abort controller for stopping the operations of the plurality of units when the error detecting section detects the error;
    a restart command receiver for receiving an instruction for restarting the measurement operations after the measurement abort controller stops the measurement operations; and
    a remeasurement controller for moving the plurality of units to initial positions thereof and then controlling the plurality of units and the detecting section so as to restart the measurement operations when the restart command receiver receives the instruction for restarting the measurement operations.

2. The analyzer according to claim 1, further comprising:
    a display section,
    wherein the restart command receiver displays a button on the display section to receive the instruction for restarting the measurement operations from a user.

3. The analyzer according to claim 2,
    wherein the restart command receiver receives the instruction for restarting the measurement operations from the user via the button.

4. The analyzer according to claim 1, further comprising:
a display section; and
display controller for displaying the content of the error and a method for error recovery on the display section when the error detecting section detects the error,
wherein the display controller erases from the display section the content of the error and the method for error recovery displayed on the display section when the restart command receiver receives the instruction for restarting the measurement operations.

5. The analyzer according to claim 1,
wherein the measurement abort controller controls the plurality of units so as to continue the measurement operations for a measuring specimen on which the measurement operations can be continued and stop the measurement operations for a measuring specimen on which the measurement operations cannot be continued when the error detecting section detects the error, and
wherein the restart command receiver is able to receive the instruction for restarting the measurement operations when the measurement operations are performed for the measuring specimen on which the measurement operations can be continued.

6. The analyzer according to claim 1,
wherein the remeasurement controller moves the plurality of units to the initial positions thereof and controls the plurality of units and the detecting section so as to restart the measurement operations after the measurement operations for a measuring specimen on which the measurement operations can be continued are stopped when the restart command receiver receives the instruction for restarting the measurement operations during the time that the measurement operations for the measuring specimen on which the measurement operations can be continued are continued.

7. The analyzer according to claim 1, further comprising:
a discarding section for discarding a reaction container where detecting the predetermined component is completed by the detecting section,
wherein the plurality of units include a reaction container holding section for holding a plurality of the reaction containers and a discarding mechanism section for discarding a reaction container to the discarding section from the reaction container holding section, and
wherein when the restart command receiver receives the instruction for restarting the measurement operations, the remeasurement controller moves the plurality of units to the initial positions thereof and then discards the reaction container held in the reaction container holding section to the discarding section by the discarding mechanism section and controls the reaction container holding section and the discarding mechanism section so as to restart the measurement operations.

8. The analyzer according to claim 7,
wherein the plurality of units includes a drive source for rotating and moving the reaction container holding section on a substantially horizontal surface by a predetermined angle in a predetermined cycle, and
wherein the remeasurement controller controls the drive source such that a cycle of rotating and moving the reaction container holding section by a predetermined angle when the reaction container is discarded is shorter than a cycle of rotating the reaction container holding section by a predetermined angle when the measurement is performed.

9. A method of restarting sample measurement by an analyzer including a plurality of units, the method comprising:

(a) receiving, by an analyzer, an instruction for staring measurement operations including preparing a measuring specimen and detecting a predetermined component from the measuring specimen;
(b) performing, by the analyzer, the measurement operations by the plurality of units when the instruction for staring the measurement operations is received;
(c) detecting, by the analyzer, an error in operations of the plurality of units during the measurement operations;
(d) stopping, by the analyzer, the measurement operations when the error is detected in the operations of the plurality of units;
(e) receiving, by the analyzer, an instruction for restarting the measurement operations; and
(f) moving, by the analyzer, the plurality of units to initial positions thereof and restarting the measurement operations when the instruction for restarting the measurement operations is received.

10. The method of restarting sample measurement according to claim 9, further comprising:
(g) displaying a button on a display section to receive the instruction for restarting the measurement operations,
wherein the step (e) is performed by receiving the instruction for restarting the measurement operations via the button displayed in the step (g).

11. The method of restarting sample measurement according to claim 9, further comprising:
(h) displaying the content of the error and a method for error recovery on the display section when the error is detected in the operations of the plurality of units in the step (c),
(i) erasing the content of the error and the method for error recovery displayed on the display section when the instruction for restarting the measurement operations is received in the step (e).

12. The method of restarting sample measurement according to claim 9,
wherein the step (d) includes a step of continuing the measurement operations for a measuring specimen on which the measurement operations can be continued and stopping the measurement operations for a measuring specimen on which the measurement operations cannot be continued when the error is detected in the operations of the plurality of units in the step (c), and
wherein the step (e) includes a step of receiving the instruction for restarting the measurement operations when the measurement operations are performed for the measuring specimen on which the measurement operations can be continued.

13. The method of restarting sample measurement according to claim 9,
wherein the step (f) includes a step of moving the plurality of units to the initial positions thereof and restarting the measurement operations after the measurement operations for a measuring specimen on which the measurement operations can be continued are stopped when the step (e) is performed during the time that the measurement operations for the measuring specimen on which the measurement operations can be continued are continued.

14. The method of restarting sample measurement according to claim 9, further comprising:
(i) discarding to a discarding section a reaction container containing the measuring specimen of which the predetermined component is detected by the detecting section, wherein the step (f) includes a step of moving the plurality of units to the initial positions thereof and then discarding the reaction container to the discarding section from a reaction container holding section and restarting the measurement operations when the instruction for restarting the measurement operations is received in the step (e).

15. The method of restarting sample measurement according to claim 14,
wherein the step (f) includes a step of rotating and moving the reaction container holding section by a predetermined angle in a cycle shorter than a cycle of the step (b) when the instruction for restarting the measurement operations is received in the step (e) and the reaction container present in the reaction container holding section is discarded.

16. An analyzer comprising:
a specimen preparing section for preparing a measuring specimen including a specimen and a reagent, the specimen preparing section including a plurality of units performing predetermined operations;
a detecting section for detecting a predetermined component from the measuring specimen prepared by the specimen preparing section;
an error detecting section for detecting an error in the operations of the plurality of units; and
a controller, including a memory under control of a processor, the memory storing instructions enabling the processor to carry out operations, comprising:
(a) receiving an instruction for starting measurement operations including preparing the measuring specimen and detecting the predetermined component from the measuring specimen;
(b) performing the measurement operations by the plurality of units when the instruction for starting the measurement operations is received;
(c) stopping the measurement operations when the error is detected in the operations of the plurality of units;
(d) receiving an instruction for restarting the measurement operations; and
(e) moving the plurality of units to initial positions thereof and restarting the measurement operations when the instruction for restarting the measurement operations is received.

17. The analyzer according to claim 16, further comprising:
a display section,
wherein the step (d) includes a step of displaying a button on the display section to receive the instruction for restarting the measurement operations from a user.

18. The analyzer according to claim 17,
wherein the step (d) is performed by receiving the instruction for restarting the measurement operations from the user via the button.

19. The analyzer according to claim 16, further comprising:
a display section,
wherein the instructions further comprising:
(f) displaying the content of the error and a method for error recovery on the display section when the error detecting section detects the error in the step (c); and
(g) erasing the content of the error and the method for error recovery displayed on the display section when the instruction for restarting the measurement operations is received in the step (d).

20. The analyzer according to claim 16,
wherein the step (c) includes a step of controlling the plurality of units so as to continue the measurement operations for a measuring specimen on which the measurement operations can be continued and stop the measurement operations for a measuring specimen which cannot be continued in the measurement operations when the error detecting section detects the error, and
wherein the step (d) includes a step of receiving the instruction for restarting the measurement operations when the measurement operations are performed for the measuring specimen on which the measurement operations can be continued.

* * * * *